United States Patent
DaCosta et al.

(10) Patent No.: US 11,727,560 B2
(45) Date of Patent: Aug. 15, 2023

(54) WOUND IMAGING AND ANALYSIS

(71) Applicant: MOLECULIGHT INC., Toronto (CA)

(72) Inventors: Ralph DaCosta, Toronto (CA); Todd E. Meaney, Thornhill (CA); Todd Daynes, Aurora (CA); Garrett R. Vermey, Toronto (CA); Liis Teene, Toronto (CA); Danielle C. Dunham, Toronto (CA); Kamyar Abhari, Toronto (CA); Steven McFadden, Toronto (CA)

( * ) Notice: Subject to any disclaimer, the term of this patent is extended or adjusted under 35 U.S.C. 154(b) by 325 days.

(21) Appl. No.: 16/966,591

(22) PCT Filed: Jan. 15, 2019

(86) PCT No.: PCT/CA2019/000002
§ 371 (c)(1),
(2) Date: Jul. 31, 2020

(87) PCT Pub. No.: WO2019/148265
PCT Pub. Date: Aug. 8, 2019

(65) Prior Publication Data
US 2020/0364862 A1 Nov. 19, 2020

Related U.S. Application Data

(60) Provisional application No. 62/625,611, filed on Feb. 2, 2018.

(51) Int. Cl.
G06K 9/00 (2022.01)
G06T 7/00 (2017.01)
(Continued)

(52) U.S. Cl.
CPC .......... *G06T 7/0012* (2013.01); *A61B 5/0077* (2013.01); *A61B 5/444* (2013.01);
(Continued)

(58) Field of Classification Search
None
See application file for complete search history.

(56) References Cited

U.S. PATENT DOCUMENTS

| 9,042,967 B2 | 5/2015 | DaCosta et al. |
| 10,438,356 B2 | 10/2019 | DaCosta |

(Continued)

FOREIGN PATENT DOCUMENTS

| JP | 2017524935 | 8/2017 |
| WO | 2004025556 | 3/2004 |
| WO | 2015/116823 A1 | 8/2015 |

OTHER PUBLICATIONS

DaCosta: "Point-of-Care Autofluorescence Imaging for Real-Time Sampling and Treatment Guidance of Bioburden in Chronic Wounds: First-in-Human Results" PLOS One, Published: Mar. 19, 2015, pp. 1-23. (Year: 2015).*

(Continued)

*Primary Examiner* — Wei Wen Yang
(74) *Attorney, Agent, or Firm* — Jones Robb, PLLC

(57) ABSTRACT

Given a specific imaging device and systems further described herein, wound characteristics of a wound fluoresce with a unique spectral signature when subjected to excitation light with a known wavelength or range of wavelengths. Images captured therefrom are subject to analyses of pixels thereof, with a plurality of training images having known wound sizes and characteristics marked-up thereon being used to generate training data, which is subsequently used to identify wound characteristics from test images in real time. Wound sizes, boundaries, bacterial presence, and other characteristics may be quantified and graphically represented as an overlay on the original wound image along with documentation related to the wound.

46 Claims, 16 Drawing Sheets

(51) Int. Cl.
| | | |
|---|---|---|
| *A61B 90/00* | (2016.01) | |
| *G06T 7/564* | (2017.01) | |
| *G06T 7/136* | (2017.01) | |
| *G06T 7/44* | (2017.01) | |
| *G06T 7/62* | (2017.01) | |
| *G06T 7/11* | (2017.01) | |
| *A61B 5/00* | (2006.01) | |
| *G06T 5/40* | (2006.01) | |

(52) U.S. Cl.
CPC .............. *A61B 5/445* (2013.01); *A61B 90/39* (2016.02); *G06T 5/40* (2013.01); *G06T 7/11* (2017.01); *G06T 7/136* (2017.01); *G06T 7/44* (2017.01); *G06T 7/564* (2017.01); *G06T 7/62* (2017.01); *G06T 2207/20081* (2013.01); *G06T 2207/20182* (2013.01); *G06T 2207/30096* (2013.01)

(56) References Cited

U.S. PATENT DOCUMENTS

| | | | | |
|---|---|---|---|---|
| 2015/0150457 | A1* | 6/2015 | Wu | A61B 5/445 600/425 |
| 2017/0231550 | A1* | 8/2017 | Do | G06T 7/11 382/128 |
| 2017/0236281 | A1 | 8/2017 | DaCosta | |
| 2018/0279943 | A1* | 10/2018 | Budman | A61B 5/445 |

OTHER PUBLICATIONS

First Examination Report dated Jun. 6, 2022 in related IN Application No. 202017036566, 8 pages.

Kumar et al., "Wound Image Analysis Using Contour Evolution," I.J. Image, Graphics and Signal Processing 6:36-42 (2014) pub online May 2014 in MECS (http://www.mecs-press.org/).
PCT/CA2019/000002, Written Opinion / International Search Report (dated Mar. 29, 2019).
Rother, et al., "'GrabCut' Interactive Foreground Extraction Using Iterated Graph Cuts," ACM Transactions on Graphics (TOG), 23:3:309-314 (Aug. 1, 2004).
Veredas et al., "Efficient detection of wound-bed and peripheral skin with statistical colour models", Medical and Biological Engineering and Computing, Springer, vol. 53, Jan. 7, 2015 pp. 345-359.
Rangayyan R. M. et al., "Segmentation of Color Images"., Color Image Processing with Biomedical Applications, Jul. 22, 2011 (Jul. 22, 2011), SPIE, 1000 20th Street, Bellingham, WA 98227-0010 USA, XP055844554, 80 pages.
Veredas et al., "Binary Tissue Classification on Wound Images With Neural Networks and Bayesian Classifiers", IEEE Transactions in Medical Imaging, vol. 5, No. 2, Feb. 3, 2010 (Feb. 3, 2010), 18 pages.
Sony Corporation., "Importing Images from Cyber-shot to your Windows PC,How to use (Windows) PlayMemories Home Support Sony", Jan. 17, 2018 (Jan. 17, 2018), URL:https://web.archive.org/web/2018011700 1019/https://support.d-imaging.sony.co.jp/ www/disoft/int/playmemories-home/en/operat ion/import-dsc.html, 8 pages.
European Search Report dated Sep. 27, 2021 related to EP Application No. EP19748362, 16 pages.
Office Action dated Jun. 29, 2022 in related CA application No. 2,955,976.
Office Action dated Jan. 10, 2023 in related JP application No. 2020-541966.
Kumar et al."Wound Image Analysis Using Contour Evolution" I. J Image Graphics and Signal Processing, Published May 2014 vol. 6, http://www.mees-press.org/, 36-42 pages.

* cited by examiner

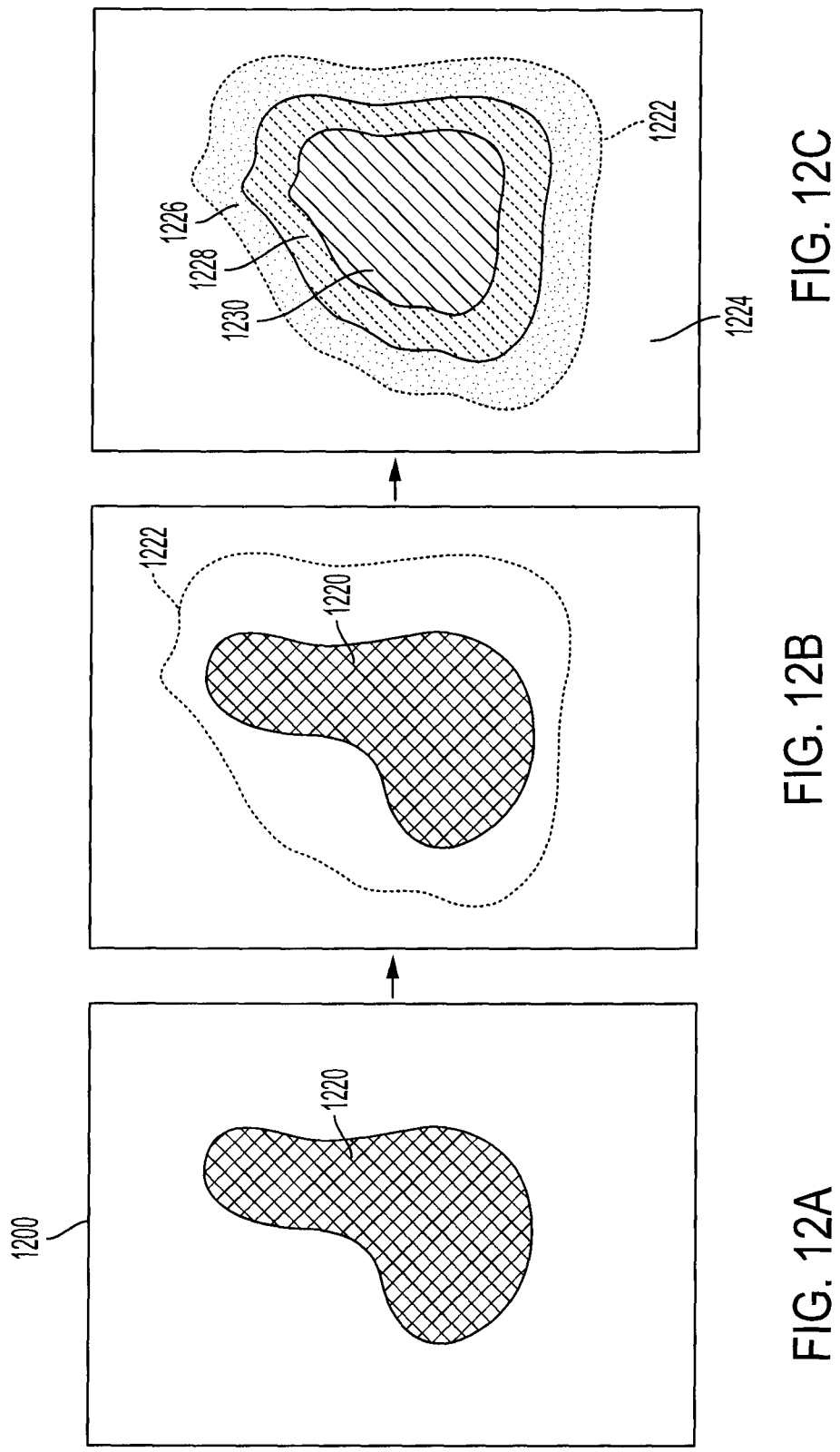

WOUND IMAGING AND ANALYSIS

This application is a U.S. national stage application under 35 U.S.C. § 371(c) of International Application No. PCT/CA2019/000002, filed Jan. 15, 2019, which claims the benefit of priority to U.S. Provisional Application No. 62/625,611, filed Feb. 2, 2018, the entire content of each of which is incorporated by reference herein.

BACKGROUND

Technical Field

A device and method for fluorescence-based imaging and monitoring is disclosed. In particular, the device and method may be suitable for monitoring biochemical and/or biological and non-biological substances, such as in wound assessment and wound care management, for both human and animal applications.

Background

Wound care is a major clinical challenge. Healing and chronic non-healing wounds are associated with a number of biological tissue changes including inflammation, necrosis, production of exudate, bleeding, proliferation, remodeling of connective tissues and, a common major concern, bacterial presence, growth and infection. A proportion of wound infections are not clinically apparent and contribute to the growing personal, emotional, and economic burdens associated with wound care, especially in aging populations. For example, *Pseudomonas aeruginosa* and *Staphyloccocus aureus* are genera of bacteria that are prevalent in hospital settings and are common causes of bacterial infection. Currently, the clinical gold standard of wound assessment includes direct visual inspection of the wound site under white light illumination for classical signs and symptoms of infection. This is often combined with a swab culture or tissue biopsy sample for laboratory testing.

However, these results are often delayed, costly, and yield insensitive bacteriological results. This may affect the timing and effectiveness of treatment. Qualitative and subjective visual assessment only provides a gross view of the wound site, but does not provide information about underlying biological, biochemical, and molecular changes that are occurring at the tissue and cellular level. Moreover, bacteria are invisible to the unaided eye, resulting in suboptimal wound sampling and an inability to appropriately track changes in bacterial growth in the wound site. This can impede healing and timely selection of the optimum antimicrobial treatment. A relatively simple and complementary method that exploits biological and molecular information to improve the early identification of such occult changes in the wound site is desirable in clinical wound management. Early recognition of high-risk wounds (e.g. containing clinically significant bacterial presence or "load") may prompt earlier treatment, guide therapeutic interventions, and provide treatment response monitoring over time, thus greatly reducing both morbidity and mortality due especially to chronic wounds.

SUMMARY

The subject disclosure solves the above-identified problems by presenting devices, systems, and computer-implemented methods that identify spectral wavelength signatures and other information indicative of wound characteristics and changes thereof in real time, perform analyses on the identified information, and output results to a user of a wound monitoring device or system. Wound characteristics include wound size, wound boundaries, wound depth, wound temperature, changes in tissue and cellular wound components, vascularization, necrosis, and bacterial presence therein. Other characteristics identified include characteristics of excised tissue, such as cancerous tissue (e.g., lumpectomy for breast cancer surgery). In use with excised tissue, the devices and methods could be used to identify characteristics such as, for example, tissue components, tumor size, tumor edge, tumor boundaries, and tissue vascularization.

In one exemplary embodiment, the subject disclosure provides a computer-implemented method for wound analysis, the computer-implemented method stored on a computer-readable medium and comprising logical instructions that are executed by a processor to perform operations comprising receiving an image of a wound, the image comprising a plurality of pixels, determining at least one area of interest in the image based on at least an application of a chroma mask to the plurality of pixels, the chroma mask being based on a histogram of pixel values, determining one or more contours of the at least one area of interest, and generating an output image comprising the one or more contours overlaid on the image. The area of interest comprises one or more wound characteristics.

In another exemplary embodiment, the subject disclosure provides a system comprising an imaging device, a processor coupled to the imaging device, and a memory coupled to the processor. The memory can be configured to store computer-readable instructions that, when executed by the processor, cause the processor to perform operations comprising acquiring an image of a wound using the imaging device, the image comprising a plurality of pixels, applying a chroma mask to the plurality of pixels, the chroma mask being based on a histogram of pixel values, generating a binary mask based on the application of the chroma mask, the binary mask identifying at least one area of interest on the image, detecting one or more contours of the at least one area of interest to define an area of interest, overlaying the one or more contours on the image to form a composite image identifying the at least one area of interest, and outputting the composite image to a user of the imaging device in real time, as well as saving the image in a raw or compressed format.

In yet another exemplary embodiment, the subject disclosure provides a tangible non-transitory computer-readable medium to store computer-readable code that is executed by a processor to perform operations comprising acquiring a plurality of red, green, and blue (RGB) images, utilizing a computer interface to mark known areas of interest on each of the plurality of images, the known areas of interest comprising at least one of a bacterial presence, a wound boundary, a collagen proliferation, and a wound size, converting each of the plurality of RGB images into an alternative color space. Non-limiting examples of color spaces include the CIELAB color space, hue-saturation-value (HSV), hue-saturation-lightness (HSL), hue-saturation-darkness (HSD), luma-chroma-hue (LCH), CMYK, cylindrical transformations, Luma plus chroma/chrominance, YCbCr: https://en.wikipedia.orq/wiki/YCbCr, LUV: https://en.wikipedia.orq/wiki/CIELUV, XYZ: https://en.wikipedia.orq/wiki/CIE_1931 color space, YUV: https://en.wikipedia.orq/wiki/YUV, Munsell color system, Natural Color System (NCS), Pantone Matching System (PMS), RAL, Aerospace Material Specification—Standard 595A (Supersedes (US) Federal Standard 595C), (US) Federal Standard 595C (Archive.org), British Standard Colour (BS) 381C, BS 2660, BS 5252 and BS 4800, LMS color space (long, medium, short), a perceptual color space based on the response functions of the cones in the retina of the eye, and the rg chromaticity space, used in computer vision applications. Subsequent to converting the images into the alternative color space, the operations comprise determining a histogram of values in the alternative color space for each of the plurality of RGB images, the histogram of values identifying a unique spectral signature for each of the known areas of interest, and generating a composite histogram based on the histogram of values in the alternative color space for each of the plurality of RGB images. The composite histogram is used to identify unknown areas of interest from at least one wound image in real time using a wound imaging device based on one or more unique spectral signatures.

In yet another exemplary embodiment, the subject disclosure provides a system comprising a processor and a memory coupled to the processor. The memory can be configured to store computer-readable instructions that, when executed by the processor, cause the processor to perform operations comprising receiving an image of a wound, the image comprising a plurality of pixels, applying a chroma mask to the plurality of pixels, the chroma mask being based on a histogram of pixel values and identifying at least one area of interest on the image, detecting one or more contours around the at least one area of interest, overlaying the one or more contours on the image to form a composite image identifying the at least one area of interest, outputting the composite image on a display device coupled to the processor, as well as saving the image in a raw or compressed format.

Additional objects and advantages will be set forth in part in the description which follows, and in part will be obvious from the description, or may be learned by practice of the present teachings. The objects and advantages of the present disclosure will be realized and attained by means of the elements and combinations particularly pointed out in the appended claims. It is to be understood that both the foregoing general description and the following detailed description are exemplary and explanatory only and are not restrictive of the claimed subject matter. The accompanying drawings, which are incorporated in and constitute part of this specification, illustrate exemplary embodiments of the present disclosure and together with the description, serve to explain principles of the present disclosure.

BRIEF DESCRIPTION OF THE DRAWINGS

At least some features and advantages of the present teachings will be apparent from the following detailed description of exemplary embodiments consistent therewith, which description should be considered with reference to the accompanying drawings, wherein:

FIG. 12A-12C depict an exemplary image of a wound with a user-defined boundary and foreground and background regions determined based thereon.

Figure 1:
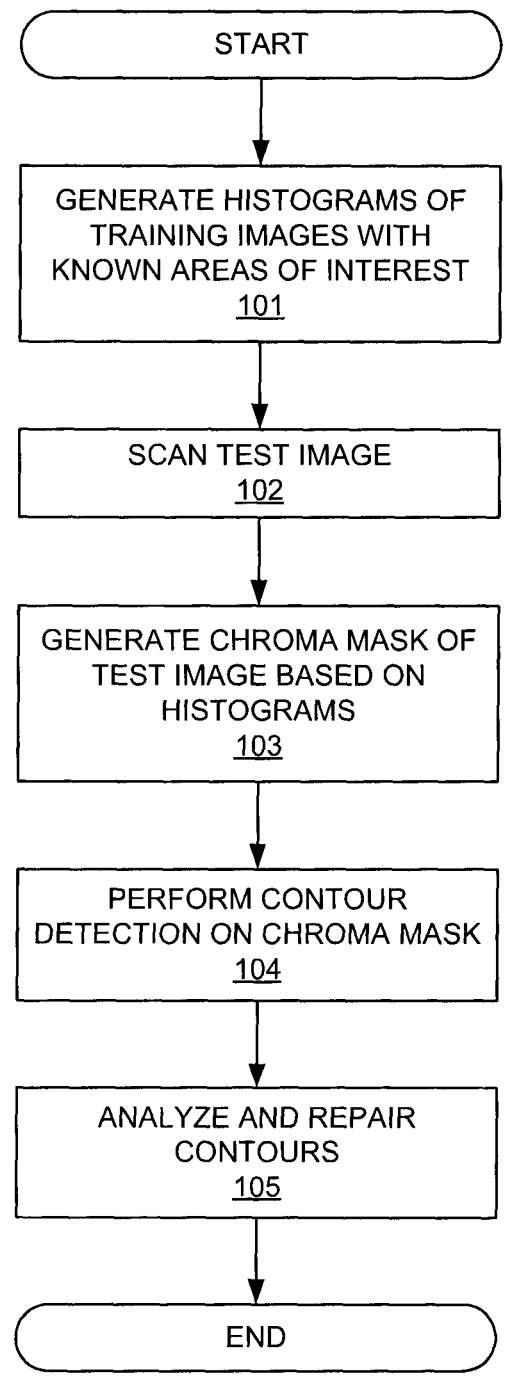
FIG. 1 depicts an exemplary method for wound imaging and analysis.

Although the following detailed description makes reference to exemplary illustrative embodiments, many alternatives, modifications, and variations thereof will be apparent to those skilled in the art. Accordingly, it is intended that the claimed subject matter be viewed broadly.

DETAILED DESCRIPTION

Reference will now be made in detail to various exemplary embodiments, examples of which are illustrated in the accompanying drawings. The various exemplary embodiments are not intended to limit the disclosure. To the contrary, the disclosure is intended to cover alternatives, modifications, and equivalents of the exemplary embodiments. In the drawings and the description, similar elements are provided with similar reference numerals. It is to be noted that the features explained individually in the description can be mutually combined in any technically expedient manner and disclose additional embodiments of the present disclosure.

The subject disclosure provides devices, systems, and computer-implemented methods that identify spectral signatures and other information indicative of wound characteristics and changes thereof in real time, perform analyses on the identified information, and output results to a user or operator of a wound monitoring device or system. Wound characteristics may include, for example, wound size, wound boundaries, wound depth, changes in tissue and cellular wound components, vascularization, necrosis, wound temperature and changes in wound temperature, and bacterial presence, distribution, and load. Although described herein with regard to use with wounds, the devices and methods disclosed herein can also be used to identify characteristics of excised tissue, such as cancerous tissue (e.g., lumpectomy for breast cancer surgery). In use with excised tissue, the devices and methods could be used to identify characteristics such as, for example, tissue components, tumor size, tumor edge, tumor boundaries, and tissue vascularization.

Exemplary wound monitoring devices described herein include hand-held/portable optical digital imaging devices having specific excitation light sources and optical band pass filters attached thereto. Using imaging devices and systems further described herein, fluorescence of components in a wound due to exposure to excitation light may be imaged and analyzed. For example, in a wound having a bacterial presence caused by or containing, for example, *Pseudomonas aeruginosa*, the *Pseudomonas aeruginosa* fluoresce with a specific spectral signature, i.e., one or more bands of wavelengths with known peaks, when subjected to excitation light. The excitation light may comprise any light with known wavelength or range of wavelengths with known peaks, such as a peak at 405 nm. Capturing and analyzing this data permits identification of bacterial presence in general, and identification of the presence of specific types of bacteria as well. In order to identify, type, and quantify the bacterial presence as well as additional characteristics of the wound, the devices and systems are trained.

Spectral information and wound size information from a plurality of training images, which are marked-up with wound sizes and bacterial presence and/or load, are used to generate training data. The training data is subsequently applied to real-time analysis of images of new wounds on a pixel-by-pixel basis, enabling identification of wound characteristics. Wound boundaries, bacterial presence, and other wound characteristics may be quantified, and graphically represented as an overlay on a white light image of a wound and surrounding healthy tissues. Further, particular types of bacteria (e.g., *Pseudomonas aeruginosa*) and/or other wound characteristics may be identified, quantified, and highlighted or otherwise indicated or overlaid on an image of the wound or images of a wound obtained over time. Other characteristics can be identified, such as characteristics of excised tissue, such as cancerous tissue (e.g., lumpectomy for breast cancer surgery), tissue components, tumor size, tumor edge, tumor boundaries, and tissue vascularization. For the purposes of this disclosure, a "real-time" operation refers to an almost-instantaneous process that occurs contemporaneously with the usage of a wound imaging device or system. For example, a user acquiring a wound image of a patient using the devices or systems described herein is provided with analysis results on a display of the same device, or a display communicatively coupled to the imaging device. The wound analysis results may be output in real-time without having to perform any additional steps and without waiting for a processing period, or in near real-time, i.e., upon the user's command. Further, the wound analysis results can be stored digitally for future access or printed as part of a clinical documentation procedure. For the purposes of the subject disclosure, the term "image" may refer to any representation of a wound, including raw pixel data or information, or any input received at a light sensor such as the cameras described herein. Moreover, analyses described herein may be performed on a series of images captured over time, or in quick succession, including frames of a video. These and additional operations are further described with respect to the embodiments depicted in FIGS. 1-13 below.

FIG. 1 depicts an exemplary method for wound imaging and analysis. Components for performing the method of FIG. 1, including devices and systems, are further described with reference to FIGS. 2-3. However, it should be noted that the operations described in FIG. 1 may be performed by any device or system, with necessary adjustments being apparent to those having ordinary skill in the art in light of this disclosure. At operation 101, histograms are generated based on training images with known areas of interest marked-up thereon. This step includes collecting or acquiring a database of clinical wound images or clinical tissue specimens (e.g., excised tissue or pathological tissue specimens). The images may have been acquired using the same device/system components that are used for real-time imaging of wounds, or at least using common imaging conditions such as an excitation (or illumination) light type and frequency, filters, etc. Further, for the purposes of the subject disclosure, a wound image or frame of a video depicts one or more wounds, surrounding tissue surfaces, and characteristics thereof. For example, a wound can include any injury or damage to a surface of an organism, such as a cut, burn, scrape, surgical incision, surgical cavity, ulcer, etc. A wound can expose an area underneath skin, including blood, connective tissue, fat tissue, nerves, muscles, bone, etc. Thus, exemplary characteristics of the wound that can be analyzed include a size of the wound, depth and/or volume of the wound (including a depth and/or a volume of a surgical cavity), edge (boundary) of the wound, presence and amounts of different types of bacteria and other organisms, amount of connective tissues, e.g., collagens and elastin, exudate, blood, bone, and so on, that are detected based on how they absorb, scatter, reflect white light and/or emit fluorescent light due to intrinsic fluorescence (autofluorescent emissions) and fluorescence from exogenous contrast agents intended to detect wound components. Exemplary characteristics of the excised tissue specimen that can be analyzed include a size of a tumor (any tumor that can be perceived/visualized by FL tumor could be partially buried, exposed to the surface, excised completely or sectioned), an edge (boundary) of a tumor in the wound, amount of connective tissues, e.g., collagens and elastin, adipose, and blood, that are detected based on how they absorb, scatter, reflect white light and/or emit fluorescent light due to intrinsic fluorescence (autofluorescent emissions) and fluorescence from exogenous contrast agents intended to detect tissue components including tumors. An example method for causing tumors to fluoresce so as to enable use of the methods and devices disclosed herein can be found in U.S. Provisional Patent Application No. 62/625,983, filed Feb. 3, 2018 and entitled "Devices, Systems, and Methods for Tumor Visualization and Removal," the entire content of which is incorporated herein by reference.

Consequently, the training images are marked with specific areas of interest by an expert having prior knowledge related to these characteristics, such as a medical professional/clinician/scientist/technician. Areas of interest can indicate general areas such as a wound boundary/edge, or specific areas such as areas containing a presence of a specific type of bacteria or other organisms, quantities or "loads" of the bacteria/organism within a wound or within an area of interest in the wound, or areas known to contain another wound characteristic of interest. Prior knowledge of bacterial presence, colonies, and/or loads thereof can be based on swab and/or tissue biopsy analyses that have positive results for specific bacterial strains. Thus, images of each type of area of interest can be acquired and separately classified depending on the target characteristic or information, including presence of known bacterial types and amounts or concentrations.

Continuing with operation 101, pixel information of the "marked-up" images is then processed and analyzed to generate histograms. Depending on the type of analysis being performed (wound size versus bacterial load or any other target information and change therein over time), the histograms can include white light and/or fluorescence data, RGB color data, and other pixel-based image information/values. Exemplary histograms are further described with reference to FIGS. 4A-4D and 5A-5D. Generally, the histograms target and classify pixel data as being inside the predefined area(s) of interest as contrasted with pixel data outside the area(s) of interest, based on a spectral signature of the pixels. Further, the training (marked-up) images can include multiple images of the same wound but having different saturations/hues/intensities values and under varying lighting conditions, so as to bolster the histograms. Such multiple training images can be used to generate a first composite histogram based on a combination of the histogram for each training image. The first composite histogram enables differentiation of areas of interest with areas of non-interest for a particular characteristic, and classification of the areas depending on the target characteristic. A second composite histogram may be generated based on a plurality of first composite histograms. The second composite histogram may be used to detect multiple different target characteristics in a test image, or similar target characteristics across multiple test images.

Each histogram comprises a number of parameters that are subsequently used in real-time processing of new images where the prior knowledge of areas of interest is not available. The parameters may be stored as a spreadsheet, lookup table, or other structure known in the art. Eventually, and as further described herein, the real-time processing operations include outputting a processed image including highlighted areas of interest as well as quantified biological and/or non-biological data such as bacteria load or wound size, among others.

At operation 102, which is generally at any point subsequent to the training operation 101, a test image is scanned for real-time analysis. The test image may be acquired in real-time using imaging hardware coupled to the analysis modules described herein. Alternatively or in addition, the test image may be acquired from said imaging hardware and transmitted to a computer that performs the disclosed operations. Alternatively or in addition, the test image may be acquired from an external source, such as a database or network. Generally, the test image is initially acquired using an RGB camera or sensor, resulting in an RGB raw image. Other systems for acquiring images in various formats are possible. For example, when excited by short wavelength light (e.g., ultraviolet or short visible wavelengths) or illuminated with monochromatic light, most endogenous biological components of tissues (e.g., connective tissues such collagens and elastins, metabolic co-enzymes, proteins, etc.) produce fluorescence of a longer wavelength, e.g., in the ultraviolet, visible, near-infrared and infrared wavelength ranges. Tissue autofluorescence imaging provides a unique means of obtaining biologically relevant information and changes therein between normal and diseased tissues in real-time and over time. Biologically relevant information includes, for example, presence of bacteria, changes in the presence of bacteria, changes in tissue composition and other factors that may enable differentiation between normal and diseased tissue states. This is based, in part, on the inherently different light-tissue interactions (e.g., absorption and scattering of light) that occur at the bulk tissue and cellular levels, changes in the tissue morphology and alterations in the blood content of the tissues. In tissues, blood is a major light absorbing tissue component (i.e., a chromophore). This type of technology is suited for imaging disease in hollow organs (e.g., GI tract, oral cavity, lungs, bladder) or exposed tissue surfaces (e.g., skin). Thus, autofluorescence imaging devices may be useful for rapid, non-invasive and non-contact real-time imaging of wounds, to detect and exploit the rich biological information of the wound to overcome current limitations and improve clinical care and management. Exemplary imaging devices and systems are further described with reference to FIGS. 2 and 3. Exemplary devices that may be used, in particular, with surgical cavities, hollow organs, and excised tissue specimens are also disclosed in U.S. Provisional Patent Application No. 62/625,983, filed Feb. 3, 2018 and entitled "Devices, Systems, and Methods for Tumor Visualization and Removal," the entire content of which is incorporated herein by reference.

At operation 103, chroma masking is performed on the image acquired at operation 102. Chroma masking enables identification of whether or not each pixel in the image is within a region defined as an area of interest or outside the area of interest, based on a spectral signature of the region. The spectral signature may be based on the alternative color space values of training-image pixels from the composite histogram generated during the training operation 101. Thus, chroma masking may be performed on pixel-by-pixel basis, and relies on the general assumption that a probability of a pixel being region of interest is higher if others in the vicinity are also in the area of interest. The output of the chroma masking operation is a binary mask that identifies "blobs" or relatively homogenous regions of pixels. Some blobs may be of interest, and other may not; thus, additional filtering operations are performed as part of the chroma masking operation 103, such as filtering sporadic outlier pixels (erosion), and biasing towards clusters of pixels (dilation). Chroma masking operations are described in further detail with reference to FIG. 6.

At operation 104, contour detection is performed on the mask generated in operation 103. Contour detection is applied to find an envelope that encloses each one of the blobs detected in the mask. This enables subsequent enumeration of areas of interest, and sorting of the areas of interest based on said enumeration. Contour detection is also subject to additional filtering, such as discarding blobs falling below a specific area threshold, or picking top 2-3 in terms of size. One exemplary method for contour detection is described in further detail with reference to FIG. 7. Another exemplary method for contour detection is described in further detail with reference to FIGS. 12A-12C.

At operation 105, repair and analysis is performed on the contours detected in operation 104. Repair and analysis may further be based on the database of pixel data collected during training operation 101, so as to identify specific issues such as portions of the contour or envelope of the area of interest that are unnatural. This may be based on a general assumption that specific biological features such as wounds, bacterial presence, etc. will not have an artificial edge, and will be more convex in shape than concave. Thus, repair and analysis assesses the performance of the chroma mask and contour detection features, and corrects any deficiencies thereof. The method ends with an output of one or more images that may comprise contours and other biological information overlaid on the original image of the wound. For example, a single output image may comprise multiple color-coded overlays. Multiple images taken over time may be overlaid, with registration algorithms and markers or stickers being used to find co-located features, to align images, identify distances, and re-orient images.

Generally, although the sequence of operations described above is based on specific experiments conducted by Applicant using the hardware described herein, other sequences of these operations may be contemplated by those having ordinary skill in the art in light of this disclosure, particularly if different hardware is used. Use of different hardware may encompass simple changes, such as changing the wavelength of excitation light or the filters used to block or remove wavelengths of light directed to the device. Such alterations would require similar changes in the training processing, as would be understood and expected by those of skill in the art.

Figure 2A:
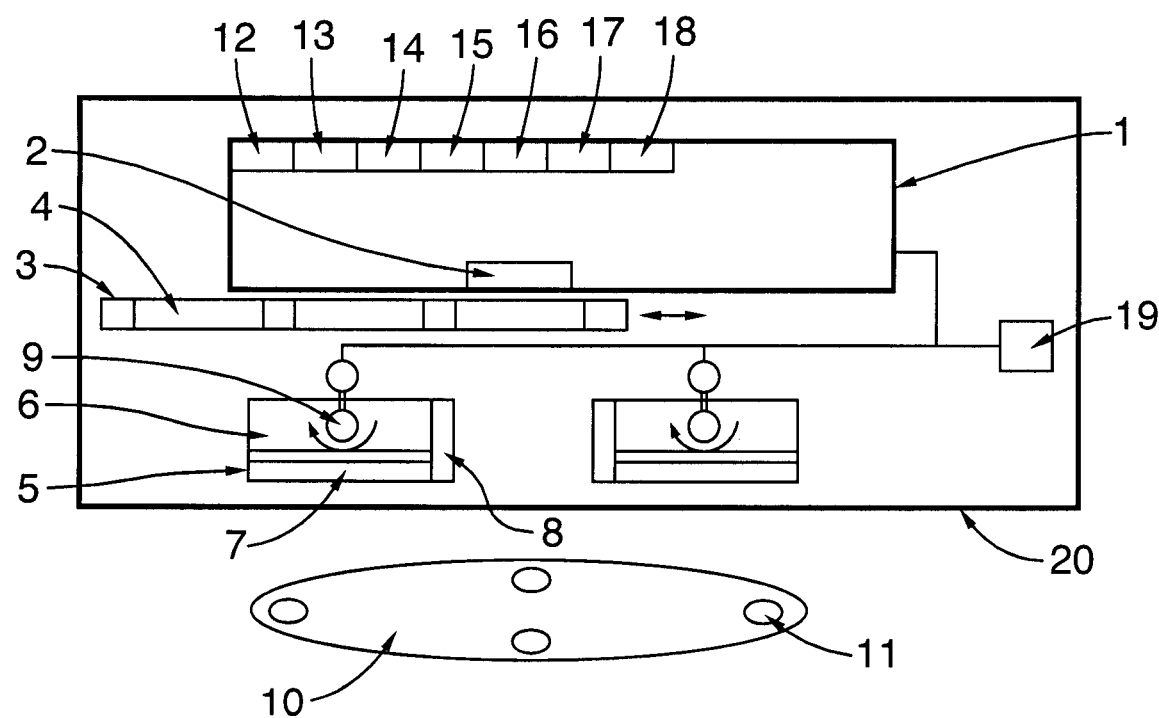
FIGS. 2A-2C depicts a schematic diagram of an exemplary device for wound imaging, analysis, and output of wound imaging analysis and documentation.
Figure 2B:
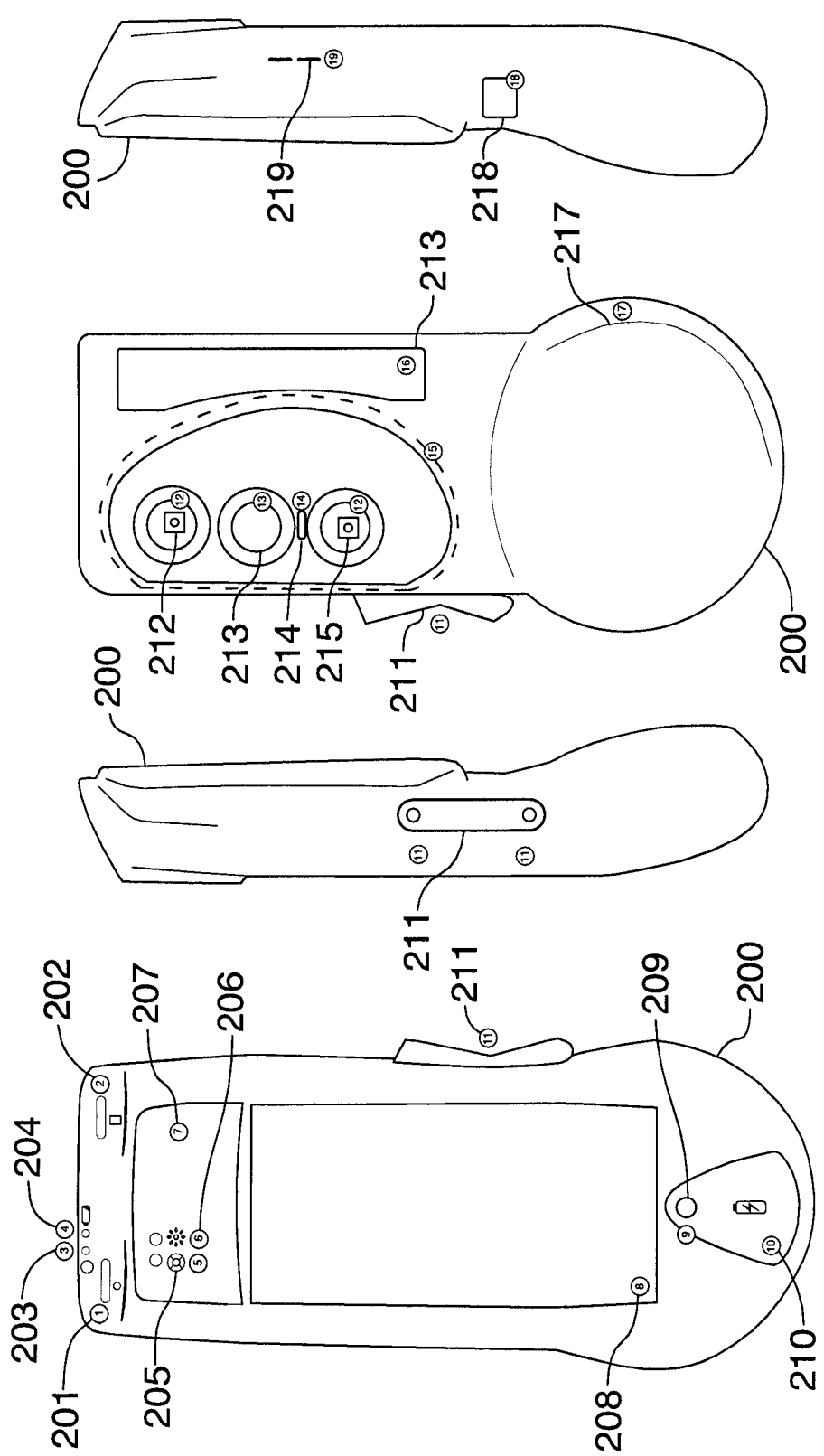
Figure 2C:
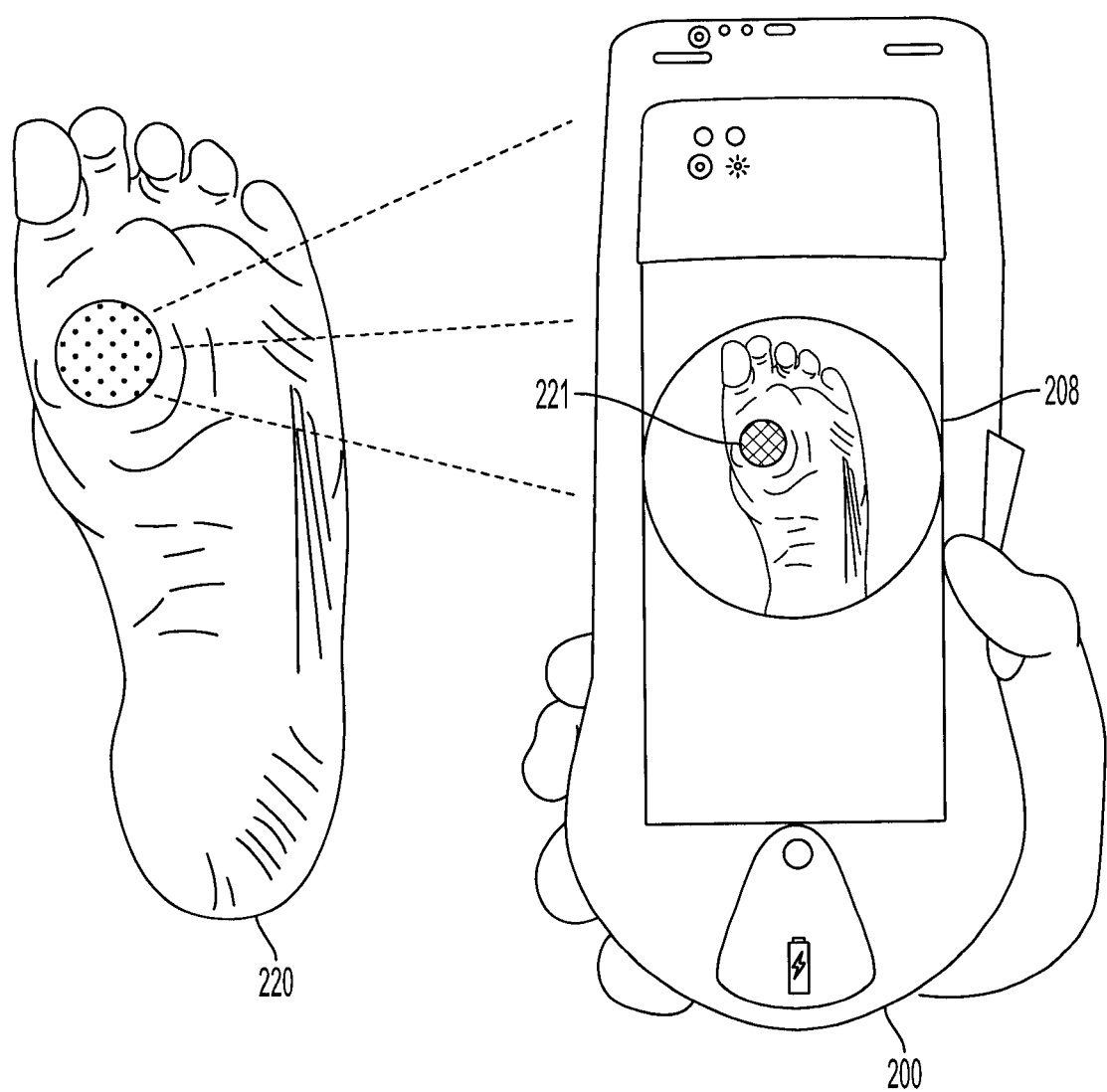

FIGS. 2A-2C depict different perspectives of an exemplary device for wound imaging and analysis. With reference to FIG. 2A, a schematic diagram is depicted for an exemplary device for wound imaging and analysis. The device is shown positioned to image a target object 10 or target surface, such as a wound on a patient. In the example shown, the device has a digital image acquisition device 1, such as digital camera, video recorder, camcorder, cellular telephone with built-in digital camera, 'Smart' phone with a digital camera, personal digital assistant (PDA), laptop/PC with a digital camera, or a webcam. The digital image acquisition device 1 has a lens 2, which may be aligned to point at the target object 10, and can detect the optical signal that emanates from the object 10 or surface. The device has an optical filter holder 3, which may accommodate one or more optical filters 4. Each optical filter 4 may have different discrete spectral bandwidths and may be band-pass or long-pass filters. These optical filters 4 may be selected and moved in from of the digital camera lens to selectively detect specific optical signals based on the wavelength of light. The digital imaging detector device may be a digital camera, for example having at least an ISO800 sensitivity, but more preferably an ISO3200 sensitivity, and may be combined with one or more optical emission filters, or other equally effective (e.g., miniaturized) mechanized spectral filtering mechanisms (e.g., acousto-optical tunable filter or liquid crystal tunable filter).

The device may include light sources 5 that produce excitation light or illumination, for example, monochromatic or white light having a wavelength peak of 400-450 nm, or any other combination of single or multiple wavelengths (e.g., wavelengths in the ultraviolet/visible/near infrared/infrared ranges), to illuminate the object 10 in order to elicit an optical signal (e.g., fluorescence). For example, the excitation/illumination light sources may be blue or violet LED arrays emitting light at about 405 nm (e.g., +/−5 nm), and may be coupled with additional band-pass filters centered at about 405 nm to remove/minimize the side spectral bands of light from the LED array output so as not to cause light leakage into the imaging detector with its own optical filters. The light source 5 may further comprise a laser diode and/or filtered lights arranged in a variety of geometries. The device may include a method or apparatus 6 (e.g., a heatsink or a cooling fan) to dissipate heat and cool the illumination light sources 5. The device may include a system or device 7 (e.g., an optical band-pass filter) to remove any undesirable wavelengths of light from the light sources 5 used to illuminate the object 10 being imaged.

The device may include a system or device 8 such as a rangefinder or other means (e.g., use of compact miniature laser diodes that emit a collimated light beam) to measure and determine the distance between the imaging device and the object 10. For example, the device may use two light sources, such as two laser diodes, as part of a triangulation apparatus to maintain a constant distance between the device and the object 10. Other light sources may be possible. The device may also use ultrasound, or a physical measure, such as a ruler, to determine a constant distance to maintain. The device may also include a structure 9 (e.g., a pivot) to permit the manipulation and orientation of the excitation light sources 5, 8 so as to position these sources 5,8 to change the illumination angle of the light striking the object 10 for varying distances.

The target object 10 may be marked with a mark 11 to allow for multiple images to be taken of the object at one time or over time and then being co-registered for analysis. The co-registration may be spatio-temporal co-registration, i.e. the images may be correlated over time as well as being correlated with a size of a mark, so as to track a change or growth of specific characteristics. The mark 11 may involve, for example, the use of exogenous fluorescence dyes of different colors that may produce multiple distinct optical signals when illuminated by the light sources 5 and be detectable within the image of the object 10. This can permit orientation of multiple images (e.g., taken over time) of the same region of interest by co-registering the different colors and the distances between them. The device itself may further include software allowing a user to control the device, including control of imaging parameters, visualization of images, storage of image data and user information, transfer of images and/or associated data, and/or relevant image analysis (e.g., detection and or diagnostic algorithms).

The digital image acquisition device 1 may further include one or more of: an interface 12 for a head-mounted display; an interface 13 for an external printer; an interface 14 for a tablet computer, laptop computer, desk top computer or other computer device; an interface 15 for the device to permit wired or wireless transfer of imaging data to a remote site or another device; an interface 16 for a global positioning system (GPS) device; an interface 17 for a device allowing the use of extra memory; and an interface 18 for a microphone. The device may include a power supply 19 such as an AC/DC power supply, a compact battery bank, or a rechargeable battery pack. Alternatively, the device may be adapted for connecting to an external power supply. The device may have a housing 20 that houses all the components in one entity. The housing 20 may be equipped with a means of securing any digital imaging device within it. The housing 20 may be designed to be hand-held, compact, and/or portable. The housing 20 may be one or more enclosures.

With reference to FIG. 2B, different views of an exemplary wound imaging and analysis device 200 are depicted. Device 200 can be, for instance, the MolecuLight i:X® device developed by MolecuLight®. Device 200 allows clinicians to quickly, safely, and easily visualize bacterial presence and distribution in skin and wounds, in real-time including but not limited to the point-of-care. Device 200 is non-contact and no imaging contrast agents are required for white light and/or fluorescence imaging. Device 200 is depicted as a handheld portable medical device comprised of a high-resolution color LCD display and touch-sensitive screen 208 with integrated optical and microelectronic components and internal battery power source. Device 200 further includes a power button 201 for turning the device on and off, a display screen power button 202 for turning display screen 208 on and off, a system status LED 203 indicating overall device performance, a battery status LED 204 indicating device battery charge, a range finder LED system 205 indicating an optimal distance from the wound being targeted or imaged, an ambient light status LED 206 for indicating an optimal lighting environment for fluorescence mode imaging, a heat sink 207 for dissipating heat as device 200 may get warm after prolonged use, a home button 209 for providing access to image and video capture functions of device 200, and a port 210 for charging and data transfer. Port 210 may be used with any universal or proprietary cable, such as USB, or a MolecuLight i:X® connecting cable.

Device 200 further includes a rocker switch 211 enabling switching between a standard imaging mode and a fluorescence imaging mode. For instance, device 200 captures real-time images (e.g., in JPG format), and videos (e.g., in MOV format) using both standard and fluorescent imaging modes. The standard imaging mode is generally used for standard photography, i.e., to capture RGB images and videos of targets illuminated with standard white light. The fluorescence imaging mode is used to capture RGB images and videos of targets illuminated with light having known peak wavelengths and intended to generate fluorescence from specific targets being excited by the light. Consequently, device 200 further includes LEDs 212 that have specific wavelengths or ranges of wavelengths for illuminating targets when in fluorescence imaging mode, as well as a camera lens 213 enabling image and video capture, a range finder sensor 214 for detecting an optimal distance from a wound or surrounding skin, and an ambient light sensor 215 for detecting optimal lighting conditions for the fluorescence imaging mode. Further, device 200 includes a holding contour 217 for allowing a user to grip the device securely, and a charging port 218 enabling device charging using a standard or proprietary power adapter.

With reference to FIG. 2C, device 200 is depicted as being used to image a wound on a patient's foot 220. Two high-efficiency LEDs of specific wavelength or range of wavelengths on device 200 illuminate the wound and surrounding healthy skin for high-resolution and real-time fluorescence imaging of bacteria and tissues, and depict the resultant image on display 208. The imaging relies on the fact that bacteria and tissue produce different levels of red and green (i.e. intrinsic) fluorescence emission wavelengths under light illumination of specific wavelengths. Unlike healthy skin, which is composed mainly of connective and adipose tissues, bacteria produce a distinct color, e.g. red or green, that is mainly caused by endogenous molecules called porphyrins which are excited to fluoresce under light illumination. Device 200 captures fluorescence emitted from both bacteria and tissues and creates a composite image on the high-resolution color LCD display 208. A user of device 200 can easily and instantly visualize the presence and location of bacteria within and around a wound, for example, as depicted by overlay 221 and document the data.

The device may be used in a typical wound care facility and integrated into the routine wound care practice allowing real-time imaging of a patient. The device may be used to image under white light illumination and/or to take fluorescence images of a wound under dimmed room lights. The device may be used in telemedicine/telehealth infrastructures, for example fluorescence images of a patient's wounds may be sent by email to a wound care specialist via a wireless communication device, such as a Smartphone at another hospital using a wireless/WiFi internet connection. Using this device, high-resolution white light and/or fluorescence images may be sent as email attachments to wound care specialists from remote wound care sites for immediate consultation with clinical experts, microbiologists, etc. at specialized clinical wound care and management centers. Exemplary wound imaging devices, their features, structures, and uses thereof are described in further detail in U.S. Pat. No. 9,042,967, entitled "Device and Method for Wound Imaging and Monitoring" and issued May 26, 2015, the contents of which are hereby incorporated by reference herein in their entirety.

Figure 3:
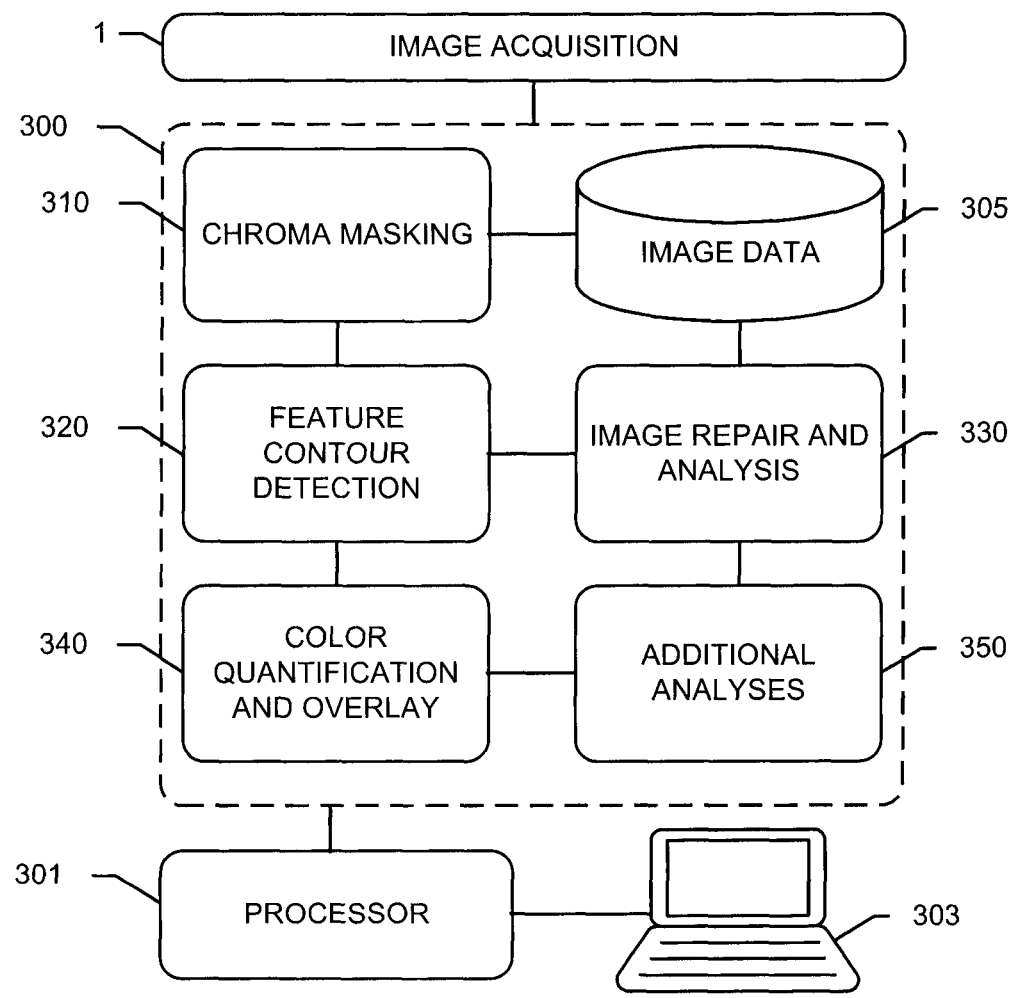
FIG. 3 depicts an exemplary system for wound imaging, analysis, and output of wound documentation.

FIG. 3 depicts an exemplary system for wound imaging and analysis. The system comprises a memory 300, which stores a plurality of processing modules or logical instructions that are executed by processor 301 in communication with a computer 303. Computer 303 may be in communication with memory 301 via a network or direct communication link. For example, memory 300 and processor 301, along with image acquisition system 1, may be part of a wound imaging device as described in FIGS. 2A-2C. In other embodiments, memory 300 and processor 301 are directly coupled to computer 303. Generally, besides processor 301 and memory 300, computer 303 can also include user input and output devices such as a keyboard, mouse, stylus, and a display/touchscreen. As will be explained in the following discussion, processor 301 executes logical instructions stored on memory 300, performing image analysis operations resulting in an output of quantitative/graphical results to a user operating computer 303.

Image acquisition 1 includes any of the imaging components described above with reference to FIGS. 2A-2C, including a camera or light sensor, light or excitation source, and appropriate optical filters or filter mechanisms. Other excitation and emission wavelengths may be used with different devices, and different pixel signatures detected. Generally, image acquisition 1 provides an image or image data of a wound in real-time, for instance by using the device of FIGS. 2A-2C to acquire an image or video (comprising a plurality of image frames) of a wound on a patient. The image and associated data is received by modules 310-350 and may be stored in database 305.

Database 305 further includes training image data from images marked with specific areas of interest by an expert having prior knowledge related to these areas of interest, such as a medical professional/clinician/scientist/technician. The training image data may be classified depending on the target characteristic, including known bacterial presence, images of known wound sizes, images of known collagen values, etc. The training image data can include histograms depicting fluorescence data, RGB color data, and other pixel values of the training images with known wound boundaries and bacterial presence. Exemplary histograms are further described with reference to FIGS. 4A-4D and 5A-5D.

Chroma masking module 103 is performed on the image acquired from image acquisition 1. Chroma masking enables identification of whether or not each pixel in the image is within the color space region defined as an area of interest, or outside the area of interest. Such a determination uses the pixel values from the composite histogram generated during the training operation, i.e. image data stored on database 305. The output of the chroma masking operation is a binary mask that identifies "blobs" or relatively homogenous regions of pixels. Chroma masking operations are described in further detail with reference to FIG. 6.

Feature contour detection module 320 is performed on the mask generated by chroma masking module 310. Contour detection is applied to find an envelope that encloses each one of the blobs detected in the mask. This enables subsequent enumeration of areas of interest, and sorting of the areas of interest based on said enumeration. Contour detection is also subject to additional filtering, such as discarding blobs falling below a specific area threshold, or picking top 2-3 in terms of size. Contour detection is described in further detail with reference to FIG. 7 and FIGS. 12A-12C.

Image repair and analysis module 330 is performed on the contours, and may also be based on image data 305, which can include specific issues that arose during the training, such as identifying unnatural portions of the contour, and correcting deficiencies of the previous modules. Repair and analysis operations are further described with reference to FIG. 8.

Color analysis and overlay module 340 generates a composite image of biological information overlaid on the original image of the wound or bacterial presence, along with color intensities based on user-defined thresholds. For example, a single output image may comprise multiple color-coded overlays. In some embodiments, an intensity of red fluorescence (or fluorescence with one or more specific wavelength peaks, i.e. a spectral signature) may be quantified, and used to indicate a bacterial presence within a given wound area. In some embodiments, this includes determining whether or not an intensity of a specific wavelength meets a threshold, upon which a determination is triggered of bacterial presence. Similarly, different intensities may be correlated with different levels of bacterial presence, whereupon a higher threshold may be used to trigger a determination of a significant infection. Color analysis is further described with reference to FIG. 10.

Additional analyses module 350 includes operations such as determining a percentage of wound area to normalize, tracking progress of wounds, comparing multiple images taken over time, registering markers and/or stickers to find co-located features and re-orient images, and so on. In some embodiments, an excitation/emission map may be stored on database 305 for a specific bacteria or other target characteristic, such as pseudomonas. The map may define, for instance, the excitation wavelength ranges that will elicit fluorescence by the target characteristic, as well as a range of emission wavelengths to be used to detect the target characteristics. The target characteristic information may be input by a user of computer 303, of a device coupled to image acquisition 1, or as part of the image data provided by image acquisition 1. Thus, additional analyses can include retrieving the correct filter and pixel information, i.e. histograms, from database 305, or instructing an operator of an imaging device to set up the device in a particular configuration that is ideal for imaging the target characteristics. Such excitation and emission information may be available for numerous types of target characteristics, as shown in Table 1 below.

TABLE 1

Fluorescence results for 9 target bacteria species

| Target | Fluorescence Emission between 600-660 nm when excited at 405 nm? |
|---|---|
| 1) *S. aureus* | Yes |
| 2) *P. aeruginosa* | Yes |
| 3) *E. coli* | Yes |
| 4) *Enterococcus* spp | Yes |
| 5) *Proteus* spp | Yes |
| 6) *Klebsiella pneumoniae* | Yes |
| 7) Coagulase-negative staphylococci | Yes |
| 8) β-hemolytic streptococci (Group B) | Yes |
| 9) *Enterobacter* spp | Yes |

Target characteristics may further include a presence of at least one of bacteria, fungus, yeast, and other microorganisms present in the illuminated portion of the wound and the area around the wound, at least one of a location, a population, a quantity, a distribution, a colonization, a contamination, a critical colonization, an infection, and an extent of at least one of bacteria, fungus, yeast, and other microorganisms when present in the illuminated portion of the wound and the area around the wound, and at least one of a presence, a location, a distribution, and an extent of at least one of collagen, elastin, connective tissue, blood, bone, exudate, stromal tissue, granulation tissue, and other tissue, cells, molecules, and fluids indicative of wound infection and/or healing present in the illuminated portion of the wound and the area around the wound. In some embodiments, in addition to *Pseudomonas aeruginosa*, bacterial presence is detected for: *Staphylococcus aureus*, *E. coli*, *Enterococcus* spp. (i.e. species within the *Enterococcus* genus), *Proteus* spp., *Klebsiella pneumoniae*, Coagulase-negative staphylococci, β-hemolytic streptococci (Group B), and *Enterobacter* spp. All of these bacteria emit fluorescence between 600-660 nm when excited under light that has a wavelength peak at 405 nm, thereby requiring no additional imaging hardware or spectral filtering. Other characteristics identified include characteristics of excised tissue, such as cancerous tissue (e.g., lumpectomy for breast cancer surgery). In use with excised tissue, the devices and methods could be used to identify characteristics such as, for example, tissue components, tumor size, tumor edge, tumor boundaries, and tissue vascularization.

In some embodiments, a significant number of pixels may indicate saturation of a specific color or combination of colors. This can result in an error in the conversion from RGB to an alternative color space. For example, when a green channel is saturated, i.e. the emission results in values greater than the maximum value of 255, this causes the hue to unnaturally shift during conversion from what is otherwise a narrow band of hue values for unsaturated colors. Consequently, an additional imaging step may discard pixels that have low saturation values. In some embodiments, this may be resolved by rapidly acquiring sequential images at varying intensities of light, and selecting an image with minimal saturation to improve detection of target characteristics or colors of interest. In other embodiments, the information lost due to saturation may nonetheless be useful in determining a particular signature for a specific type of area of interest. In other words, the fact that saturation is occurring for a particular type of wound or bacteria may be recorded and used in subsequent determinations targeting said particular type of wound or bacteria.

As described above, the modules include logic that is executed by processor 301. "Logic", as used herein and throughout this disclosure, refers to any information having the form of instruction signals and/or data that may be applied to affect the operation of a processor. Software is one example of such logic. Examples of processors are computer processors (processing units), microprocessors, digital signal processors, controllers and microcontrollers, etc. Logic may be formed from signals stored on a computer-readable medium such as memory 300 that, in an exemplary embodiment, may be a random access memory (RAM), read-only memories (ROM), erasable/electrically erasable programmable read-only memories (EPROMS/EEPROMS), flash memories, etc. Logic may also comprise digital and/or analog hardware circuits, for example, hardware circuits comprising logical AND, OR, XOR, NAND, NOR, and other logical operations. Logic may be formed from combinations of software and hardware. On a network, logic may be programmed on a server, or a complex of servers. A particular logic unit is not limited to a single logical location on the network. Moreover, the modules need not be executed in any specific order. Each module may call another module when needed to be executed.

Figure 4A:
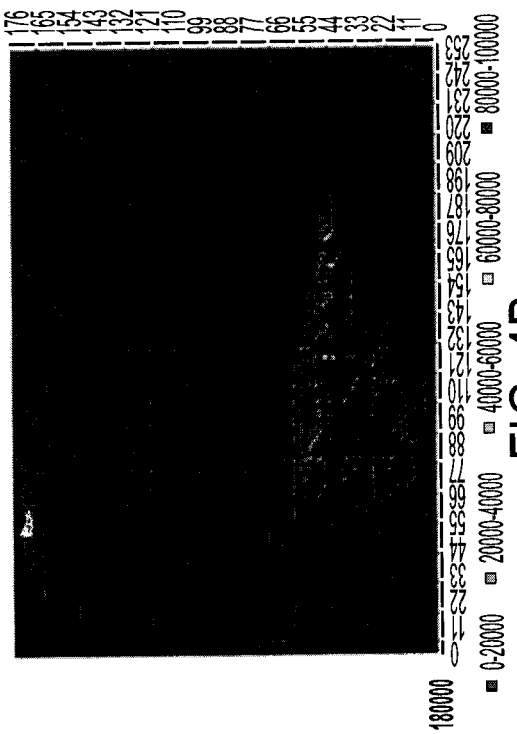
FIGS. 4A-4D depict exemplary histograms for a training image.
Figure 4B:
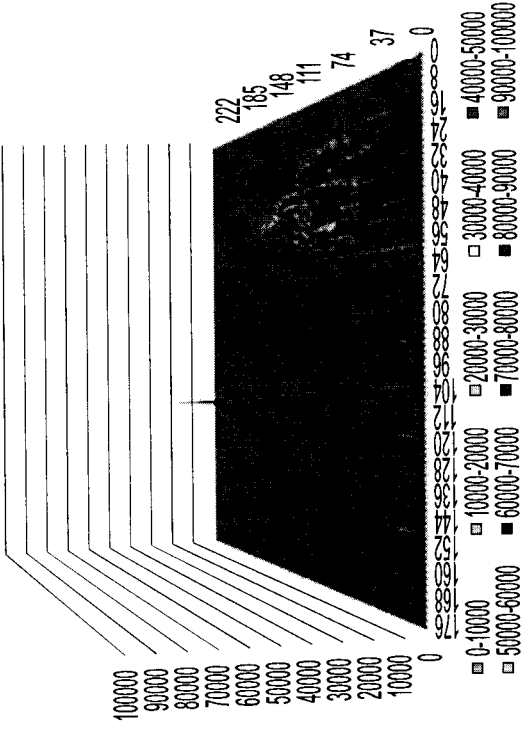

FIGS. 4A-4D depict exemplary histograms for a training image. As described herein, the histograms are used to identify exemplary hue saturation and color profiles for standard wound shapes. For example, images of fluorescence emission and/or white light reflection from known wounds and bacterial loads may be marked-up with the known information, pixel values of said images converted from RGB (red, green, blue) to HSV (hue, saturation, value) or other alternative color space as described above, and a 2D histogram of the pixels within and outside the area of interest may be generated. Further, different sets of histograms for wound size vs. bacteria may be generated, either separately or in parallel. FIG. 4A depicts a histogram for pixels within a region of interest of a single training image, and FIG. 4B depicts a histogram for pixels outside the region of interest. The illustrated histograms are plotted with saturation values from 0 to 255 on the x-axis and hue values from 0 to 179 on the y-axis. These ranges are merely exemplary, and may vary depending on a sensitivity of imaging instruments and/or the type of images being analyzed.

Figure 4C:
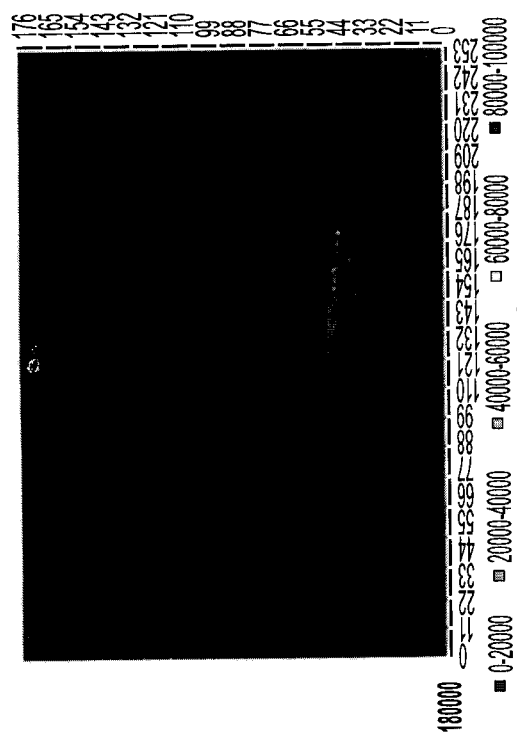
Figure 4D:
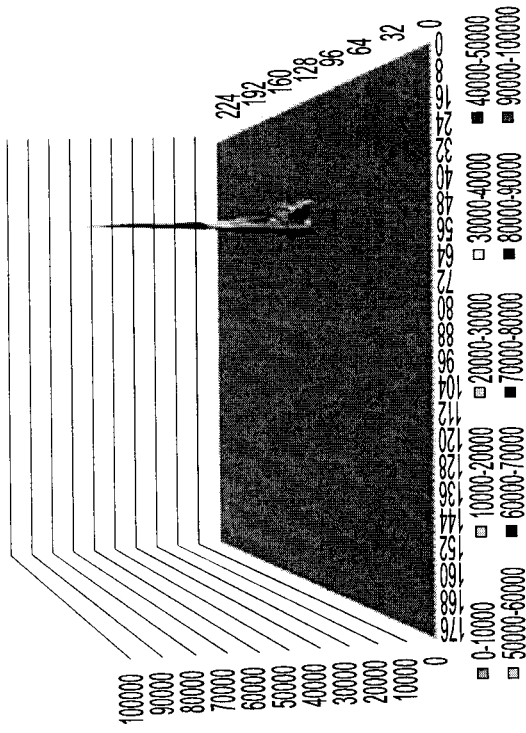
Figure 5A:
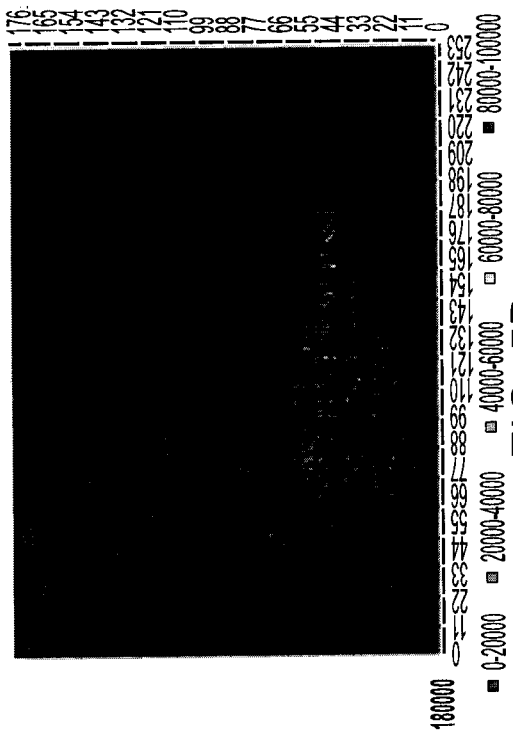
FIGS. 5A-5D depict exemplary composite histograms for a plurality of training images.
Figure 5B:
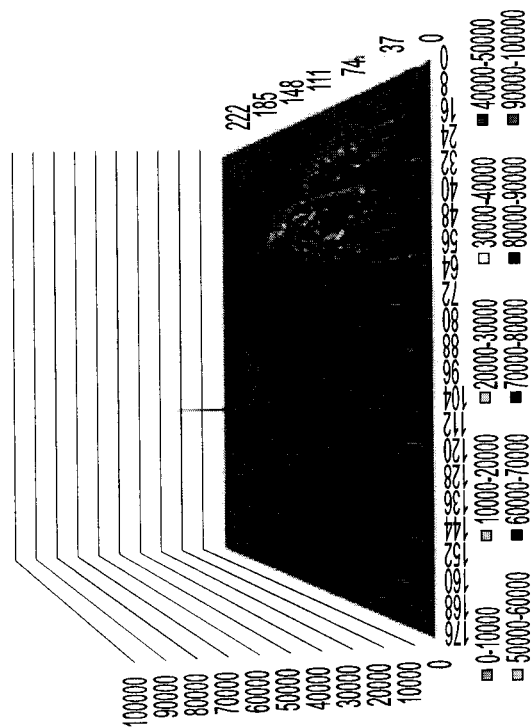
Figure 5C:
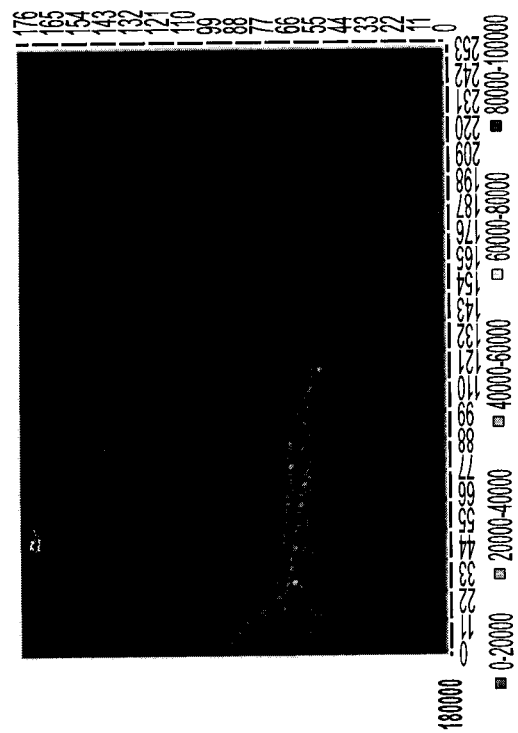
Figure 5D:
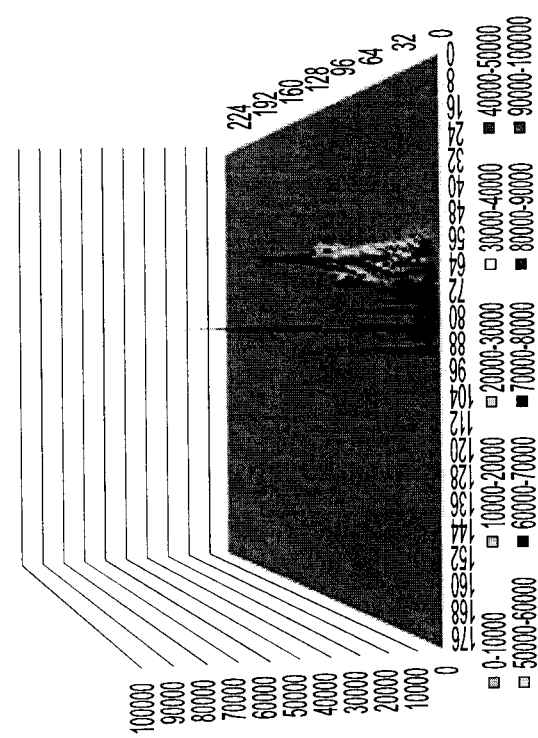

Further, the histograms of FIGS. 4A and 4B are presented from an overhead view with population density of each hue and saturation "bin" indicated by a color scale. A bin is simply a unique combination of saturation and hue values. Bins drawn in orange and yellow contain a large population of pixels. In order to plot histograms of pixels within the ROI and outside the ROI using the same population density scale, each bin frequency from the within ROI histogram is multiplied by the maximum bin frequency value from the outside ROI histogram. This process is referred to as data normalization. FIGS. 4C and 4D depict the same histograms (respectively, inside the AOI and outside the AOI), from a different perspective. It is evident from these histograms that pixels within the area of interest have a tightly grouped range of hue and saturation values versus pixels outside the area of interest.

As further described herein, after a suitable sample of images with identified region of interests have been processed, a composite histogram can be generated. FIGS. 5A-5D depict exemplary composite histograms for a plurality of training images corresponding to the histograms of FIGS. 4A-4D. This composite histogram is used to generate a suitable first pass chroma mask as described herein. Moreover, out-of-boundary behavior, such as the image saturation identified above, can be visualized through the histograms, and the real-time image analysis procedures can be developed to minimize these effects.

Figure 6:
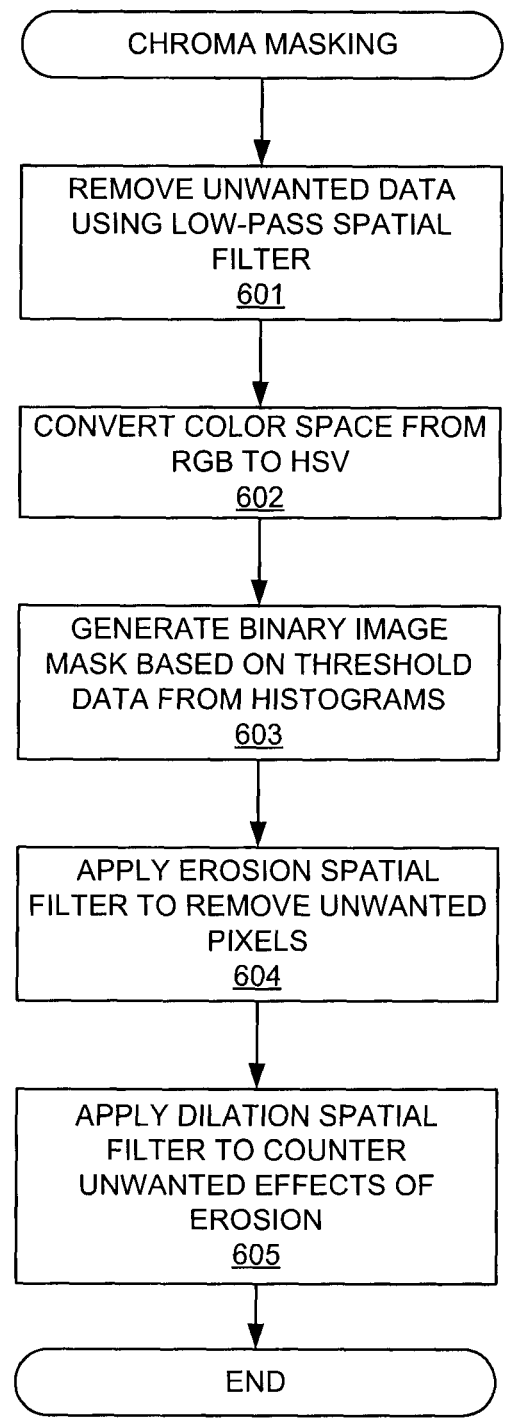
FIG. 6 depicts an exemplary method for chroma masking.

FIG. 6 depicts an exemplary method for chroma masking. The method may be performed by the components described in FIGS. 2 and 3, or by any suitable means. Chroma masking begins with removing unwanted data using a low-pass spatial filter at operation 601, which removes noise and insignificant outlier pixels. At operation 602, the image is converted from a RGB (Red/Green/Blue) color space to an alternative color space to facilitate subsequent generation of the histogram. The color space conversion uses the RGB input image sensed at the camera, whether the wound is excited with white light or with light of specific wavelengths or ranges thereof. At operation 603, a binary image mask is generated based on predetermined thresholds from the earlier training operations. In other words, the thresholds applied to the alternative color space values of the current image, resulting in a binary mask. Subsequently, at operation 604, a spatial filter is applied on the binary color mask, which has the effect of removing unwanted pixels such as outliers, and sparse segments. This is based on the theory that pixels of interest will tend to be surrounded by other pixels of interest. However, erosion may remove pixels that are actually within the area of interest, so operation 605 is performed to apply a dilation spatial filter, which counters some of the negative effects of erosion in operation 604 and has the effect of rejoining smaller clusters that survived the erosion.

Figure 7:
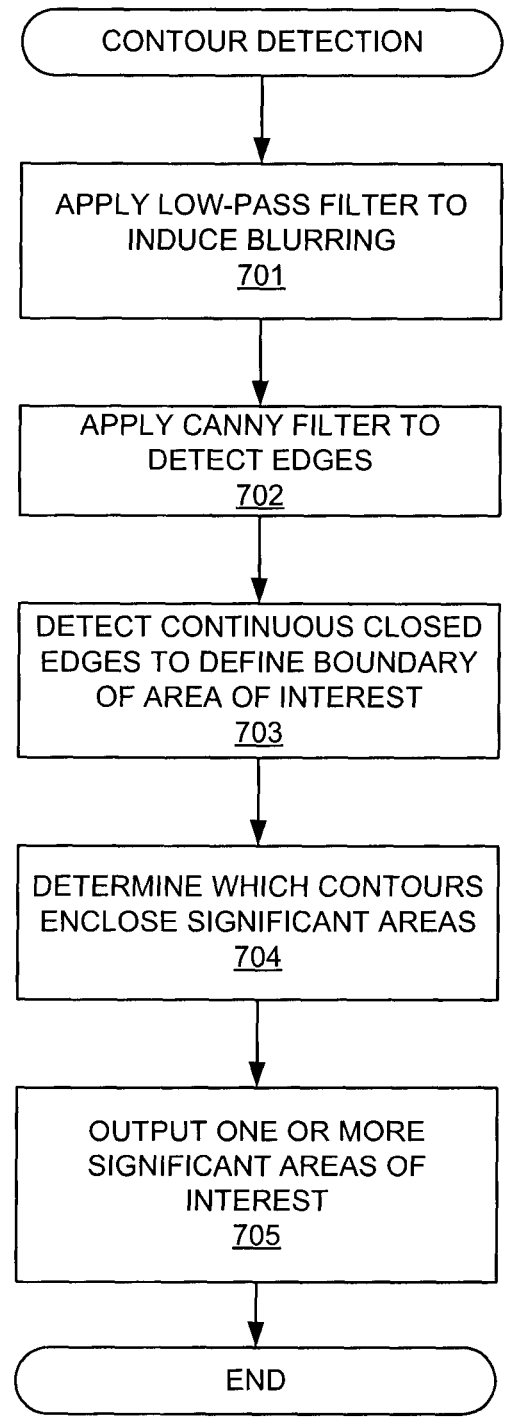
FIG. 7 depicts an exemplary method for contour detection.

FIG. 7 depicts an exemplary method for contour detection, performed subsequent to the chroma masking operations of FIG. 6. The method may be performed by the components described in FIGS. 2 and 3, or by any suitable means. The method begins at operation 701 with a low-pass filter, a processing stage which removes some of the detail in the mask, thereby inducing blurring. The blurring is combined with subsequent operation 702, i.e. a high-pass edge detection filter (Canny filter), which finds the edges of the regions identified in the chroma masking operation. Then, at operation 703, continuous closed edges are detected using contour detection. The continuously closed edges define the boundary between the pixels that are inside and outside the areas of interest. This results in a large number of closed contours of various sizes. Subsequently, the contours are analyzed in step 704 to find the contours that enclose the largest areas, i.e., those that are more likely to carry significant information. For example, the closed contours may be arranged in order of area, as described herein, and the contours enclosing the largest 2-3 areas can be selected as defining the areas of interest. This method outputs one or more of the most significant areas of interest.

Generally, the contour detection of FIG. 7 may not detect all relevant contours, or may end up eroding away contours until they are convex in shape, thereby losing useful information. For example, as erosion occurs, sometimes the wound boundary is eroded, resulting in a concave contour. As the actual shape of the wound can be very irregular with many concave regions, the image repair operations identify specific extreme concave features which could be considered unnatural. This may further be applied to bacterial presence. As erosion can discard pixels that are part of a region with bacteria, thus resulting in an abnormal contour. Further, another exemplary method for contour detection is described in further detail with reference to FIGS. 12A-12C.

Figure 8:
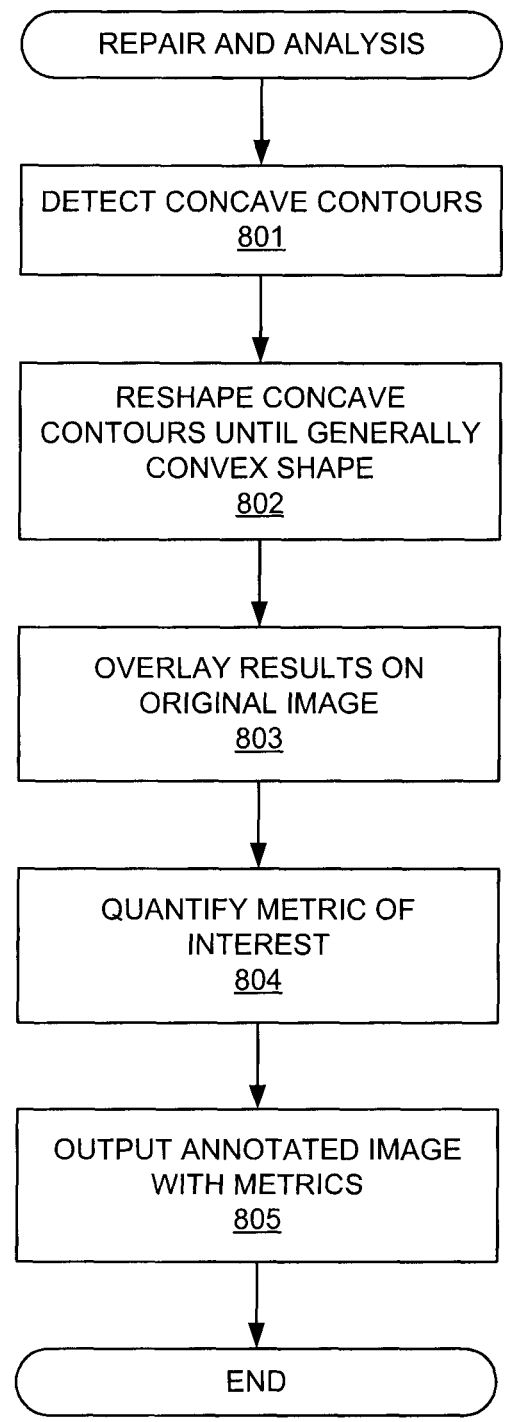
FIG. 8 depicts an exemplary method for image repair, analysis, and output of wound documentation.

FIG. 8 depicts an exemplary method for image repair and analysis. The method may be performed by the components described in FIGS. 2 and 3, or by any suitable means. The method begins at operation 801, where concave contours are detected, and a convex hull of the wound is determined. The contours are analyzed to ensure that the shape of the closed contour (enclosing the area of interest) is relatively convex in nature. If the contour exhibits features that are concave, this may be an indicator that portions of the contour detection may have been erroneous. This concept is based on the theory that many of the biological features that are being detected will typically be more convex in shape. This information may be programmed into the system based on the training information. Consequently, at 802, the erroneous concave features can be reshaped by bringing them closer to the convex hull, thus providing a more overall convex shape for the wound boundary, as depicted in FIG. 9B. Finally, at 803, 804, and 805, a final analysis provides a graphical overlay on the original data to highlight the area of interest, and performs the final quantification of the metric of interest such as bacterial load or wound size, and a composite image with overlays is output.

Figure 9A:
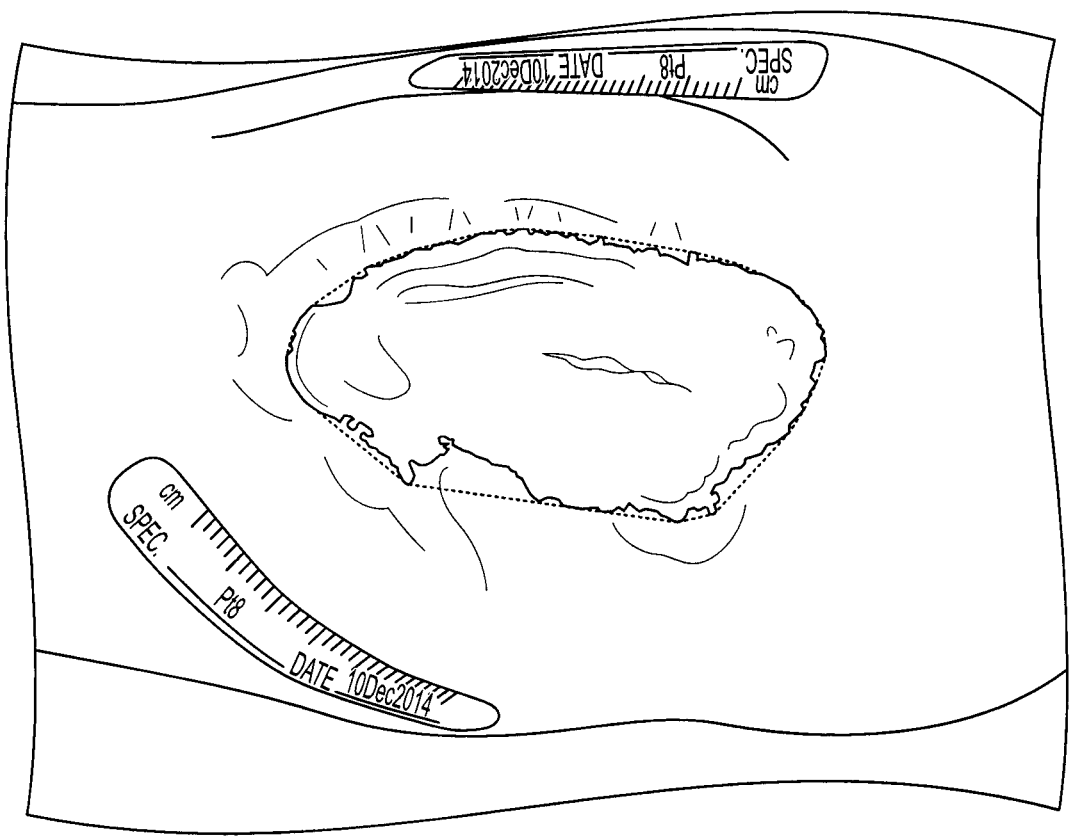
FIGS. 9A-9B depict exemplary output images of wound imaging and analysis operations.
Figure 9B:
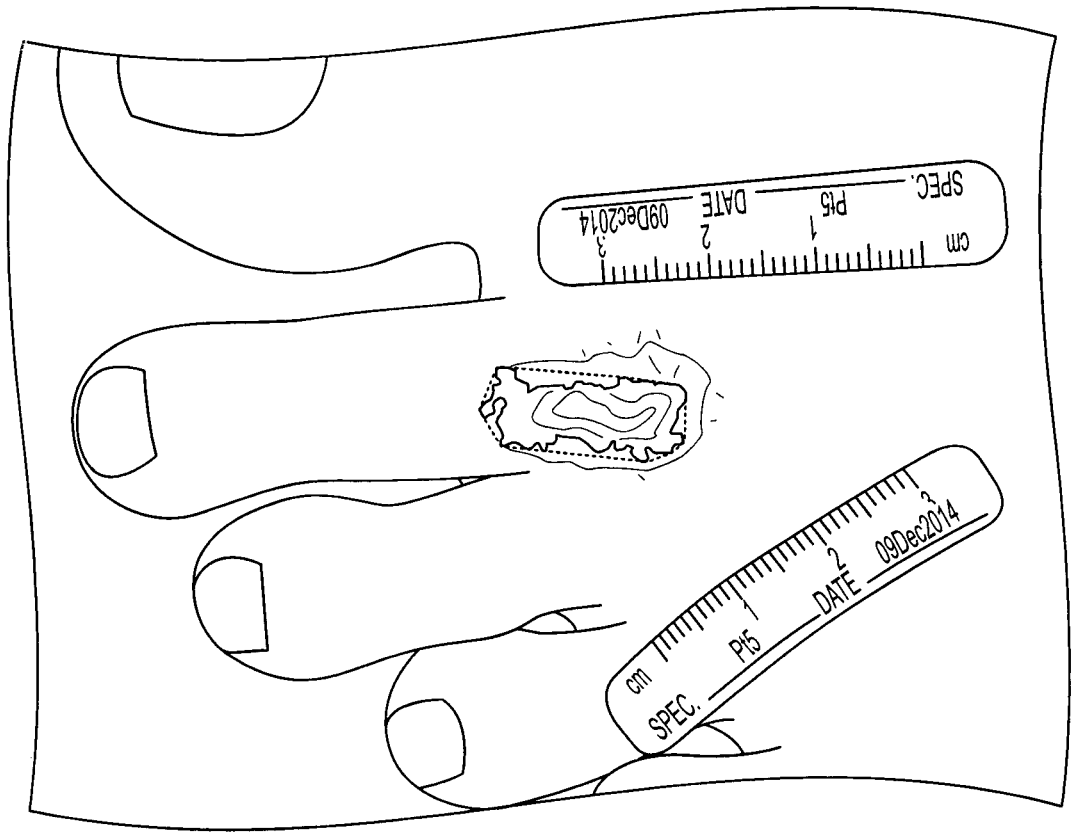

FIGS. 9A-9B depict exemplary output images of wound imaging and analysis operations. The figures show the wound boundary detected and marked with a white boundary, and the convex hull of the wound depicted by the cyan overlay around the wound. The wound area calculation presented at the top of each image is a count of the number of pixels within the wound. A target marker (or sticker of a known size, shape, color and/or pattern, or a known image, marking, or motif on it) may be attached to the patient, thereby enabling a calculation of actual wound area using a simple ratio between the known target pixel count and the detected wound pixel count. FIG. 9A depicts a white outline resulting from the original wound boundary measurement. As described in FIG. 8, the cyan overlay represents the convex hull around the wound, which is used as an intermediate calculation. The image is then repaired by detecting a significant concave feature as obtained by comparing the vector points of the white contour and the convex hull. If a significant concave feature is detected, the vector points of the wound boundary in that convex region are replaced with the vector points of the convex hull. FIG. 9B depicts the resultant reshaped wound boundary.

As described herein, these operations are used to determine numerous target characteristic information and changes therein, such as wound size, bacterial load, type(s) and presence of bacteria, and/or infection. Despite the fact that a wound image typically comprises only one wound, whereas the same (or different) image may comprise several areas of bacterial presence/growth/extent/colonies, the described modules are applicable to both wound size, depth, and bacterial detection. For example, the detected wound boundary may be a contiguous perimeter, i.e. a single connected line, and pseudomonas bacteria may exist as a variety of islands within and around the wound boundary. Thus, the erosion operation may be applicable to both the wound perimeter and to perimeters of bacterial presence. For example, upon determining contours, the operations of marking the perimeter around a region of interest may be repeated for multiple regions of interest, and eventually sorted by size of area for a final filter that may be adjustable for different applications.

Moreover, additional color and intensity determination operations may be performed on wound images. For example, some bacteria produce a red fluorescence signal when illuminated and imaged with the devices and systems described herein. To analyze the fluorescence signal(s) in the captured images, a bacterial load quantification operation may be used to identify and quantify the bacterial fluorescence signal. While described herein with reference to red fluorescence, it will be understood that the methods and analyses described could be used to analyze other colors or spectral wavelengths of fluorescence to identify bacterial load or other parameters associated with a given fluorescence wavelength.

Figure 10:
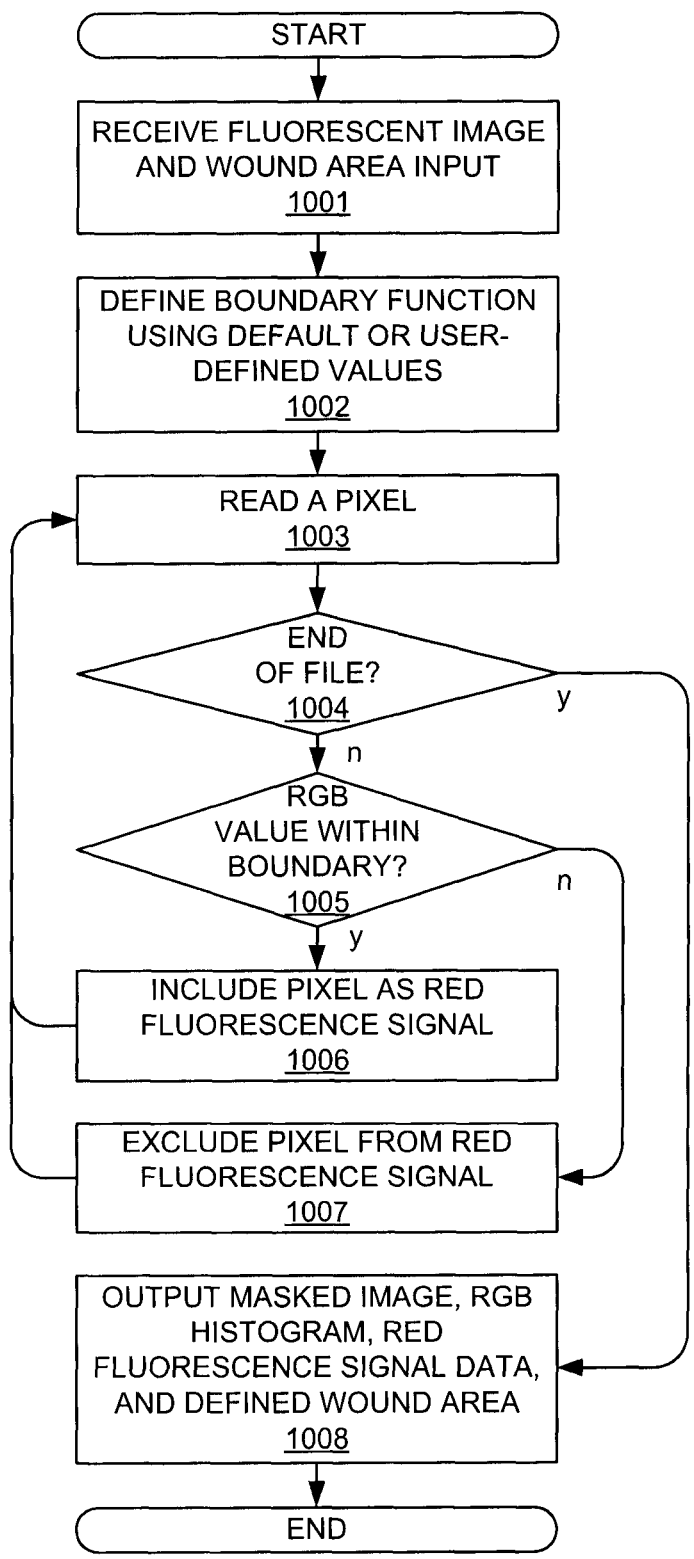
FIG. 10 depicts an exemplary method for color analysis of a wound image.

FIG. 10 depicts an exemplary method for spectral analysis of a wound image. The method begins at 1001 with receiving a fluorescent image along with an optional input of wound size input. The wound size input can be useful in determining wound progress by processing the color information as a function of wound size. In either case, the image may be a RGB (red, green, blue) color image based on the additive color model in which red, green and blue color channels are added together to produce a broad array of colors. Each pixel in a digital image has three 8-bit values (0-255) corresponding to the intensity of each individual RGB color channel, where 0 represents no color and 255 represents the true RGB color. To identify areas in the image that are red and create an image mask as a visual representation, the boundary must incorporate all three color channels. This is accomplished by defining thresholds on the RGB channels, and then using these thresholds to create a boundary of what is considered fluorescent red and what is not.

At operation 1002, thresholds for the boundary function are defined, either using default values (pre-set) or input by a user. The boundary function will represent the border on an RGB color cube that separates the accepted red colors from the rest of the colors. This border will be centered around RGB red (255, 0, 0), but the distance from RGB red to the boundary to will not be equal in all directions. There will be a greater accepted distance along the red channel than either the blue or green color channels to give greater weight to the red channel. In other words, the thresholds identify the accepted intensity for the color channel to be accepted in the resultant mask. Consequently, for detecting red fluorescence, a minimum threshold is set for the red channel, and a maximum threshold is set for the green and blue channels. Further, separate thresholds for each color channel must exist to give greater weight to the red channel when determining if the pixel is red. Since a variety of variables can affect the color of an image (brightness, saturation, hue) these thresholds are also adjustable by the user to allow for an optimal mask to be generated for the image. The resulting boundary function will be a 3D quadratic defined by three initial conditions (user defined threshold values) that represent the minimum red intensity, maximum green intensity and maximum blue intensity. Moreover, other combinations of color thresholds may be defined to generate masks of specific colors.

Operations 1003-1007 select individual pixels and determine whether or not the pixel meets the boundary conditions or thresholds defined in operation 1002. So long as there continue to be pixels left to analyze, based on determination 1004, pixels continue to be "binned", i.e. included (step 1006) or excluded (step 1007) from the red fluorescence signal output. Eventually, when there are no more pixels, the masked image is output, along with optional RGB histogram, fluorescence signal data, and a defined wound size. For example, histograms generated based on intensities of each RGB channel can be used to visually guide the user to choose appropriate threshold levels, as depicted in FIGS. 4 and 5. In other words, this operation can be an iterative process, allowing the user to adjust the thresholds in real time while viewing the output, until they are satisfied.

Further, similar to the RGB histograms, the individual RGB color channels can provide valuable information for additional image analysis. A color channel is represented by a greyscale image of the same color image, made of only one of the RGB colors. Dark areas (black) represent low intensity in the channel and bright areas (white) represent high intensity in the channel. These greyscale images are generated by outputting only the one color channel of interest when displaying the image.

Clearly defining the wound size enables additional operations, as further described above with reference to FIG. 3. For example, this enables a calculation of the area of red or other fluorescence signal(s) as a percentage of the wound size. The wound size can be defined as an input at 1001, for instance by a user selecting the periphery of the wound via a user interface. The output may be normalized as a percentage of the wound size and can be used to track healing progress. For example, changes in the bacterial load/red fluorescence can be monitored over a period of time, and determined as a percentage or rate of change of pixels per unit area of the wound. Moreover, the bacterial load (or redness) can be outside a wound size, thus enabling using the wound size as a fixed measurement, and determine a change in a relative amount of redness, thereby indicating a growth of the bacterial load. Besides wound size, any other fixed quantity can be used, such as a percentage of image size.

Further, the intensity of the red fluorescence signal can be used to quantify the bacterial load. Intensity can also be used to quantify other fluorescing element/compounds/components of the target in a wound or in a surgical field. Given the same thresholds and same imaging conditions for a series of images, histogram values of each image can be compared over time, to track changes in intensity of redness, which directly correlates to bacterial load. Thus, output 1008 can include minima, maxima, and mean intensities of the signal, as well as a histogram of the distribution for a visual representation.

Figure 11:
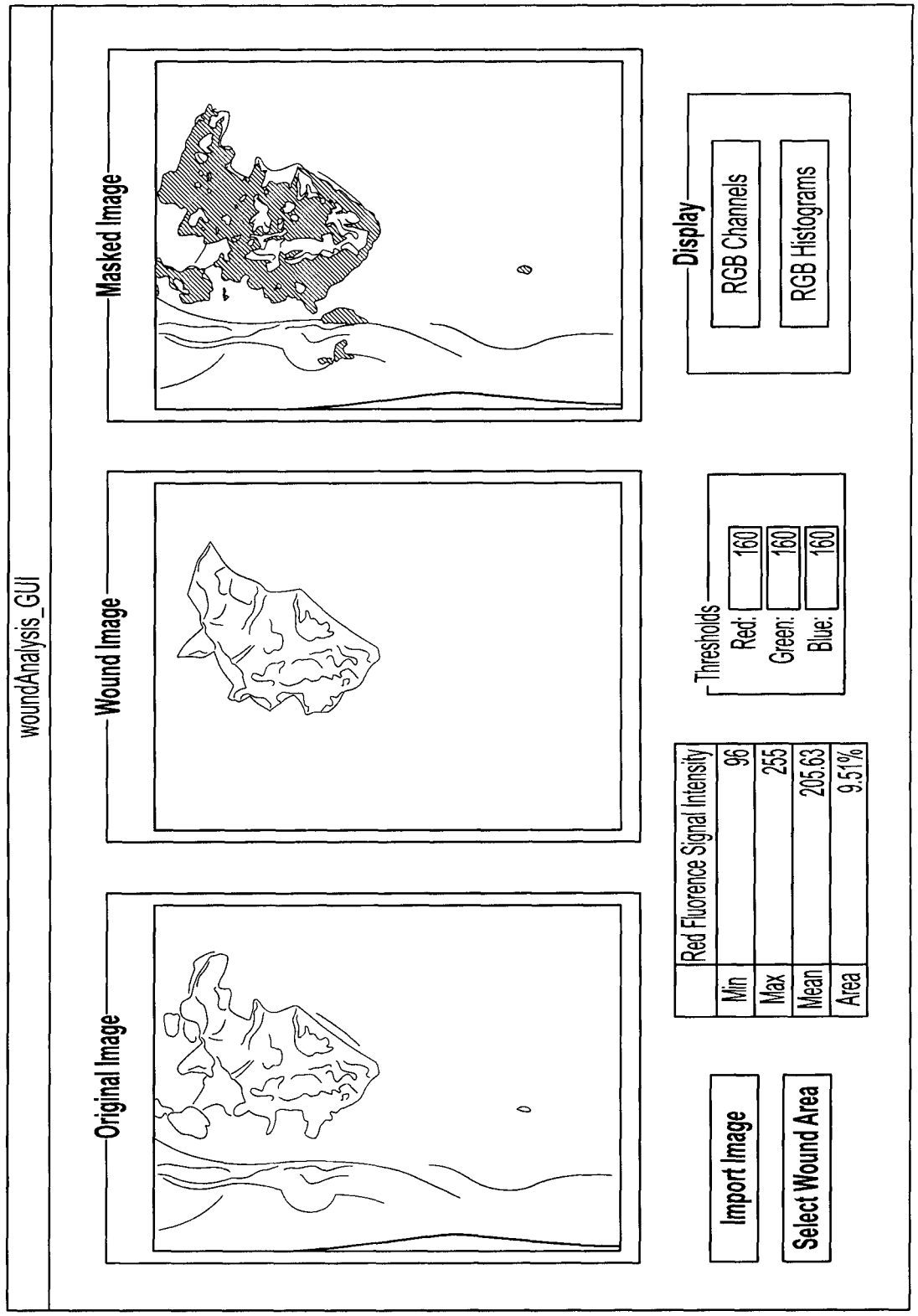
FIG. 11 depict exemplary output images and documentation of a wound image via an exemplary user interface.

As described herein, the output can be used to determine effectiveness of treatment via a marked-up image highlighting area of interest and/or overlaid on the raw/starting image. FIG. 11 depicts an exemplary user interface (GUI) for color analysis of a wound image. The GUI demonstrates the input and output of the bacterial load quantification operations described in FIG. 10. The "original image" is used for the user to define the periphery of the wound and perform the load quantification operations. The mask of red pixels is shown overlaid on the "masked image." Metrics displayed in the 'red fluorescence signal intensity' are calculated from the pixels included in the mask. The pixels included in the mask are used to calculate percentage of the wound size that is covered by bacteria. In addition, a lookup table (LUT) may be used to overlay a color on the masked pixels so as to indicate relative fluorescence intensity. FIG. 11 depicts an exemplary application of a LUT on an image, with intensities of the bacteria identified in the LUT illustrated in greyscale on the right side of FIG. 11.

Further, as described above, spatio-temporal co-registration may be performed to correlate a plurality of images to provide more detailed analyses for a specific wound, characteristic, or patient, such as tracking a change or growth of specific characteristics. For example, a device equipped with white light, fluorescent, and thermal sensors may be used to acquire simultaneous images of each type from the same target wound or characteristic. In an embodiment, a white-light reflectance image, a fluorescent image, and a thermal image of the same wound may be subject to their own respective analyses, and then used as inputs to generate a composite image with all three images and analyses overlaid thereon. This combination or super-composite output image can be used to determine additional analyses or diagnosis of the specific wound. For instance, a wound (or region thereof) with a large bacterial presence, i.e. a significant bacterial load, and depicting a high temperature or "hot-spot", may be determined to be infected, including when used in combination with standard clinical practice guidelines. In other words, analyzed data from different types of images of the same wound may be viewed concurrently, i.e. in a single post-analysis super-composite image, to determine additional information about a wound that may not be available or immediately apparent from viewing separate white-light, fluorescent, or thermal images individually.

Even deeper analyses may be performed by viewing super-composite images that are generated over a period of time for the same wound or patient, for instance by using registration markers/stickers or co-located features. In addition, simultaneously-acquired and spatially co-localized images acquired using, for instance, an imaging device with multiple sensors, may be useful to track a change in bacterial load of a specific wound over time. A total bacterial load and a difference in wound temperature vs. surrounding surface temperature can be determined over time for the same wound. Observing relationships between the change in bacterial load and the temperature can be used to trigger the determination of an infection. For example, with the knowledge that a bacterial load increases prior to the temperature rising, a relationship may be determined and used to predict occurrence or risk of infection in various situations.

Although these operations have been described with respect to red fluorescence, other colors may be used to determine other target characteristics such as a proliferation of collagen, which can provide a measure of wound healing, blood, bone, etc. It is also possible to determine target characteristics such as density of collagen, elastins and other fluorescing compounds, including those in diseased tissues like tumor, as well.

In other embodiments, the results of the spectral analysis can be used to differentiate viable tissue from non-viable tissue, for example referring to the brown or black tissue specks within the green tissue in FIG. 11. The numerous operations described herein may be combined in different ways, for example, to determine and output a wound size, and subsequently to determine or quantify a bacterial presence or other characteristic within the bounds of the wound size.

Further, these operations may be applied to 3D stereoscopic images comprising two simultaneously-acquired and longitudinally-displaced 2D images. This is enabled by generating two histograms corresponding to each of the two stereoscopic images, and performing the above-described analyses performed on each of two subsequently acquired stereoscopic images. In some embodiments, a histogram for a 2D image can be used to process a pair of stereoscopic (or 3D) images, without materially affecting the outputs.

In an exemplary embodiment, detection and measurement of the wound boundary (as described in, for instance, FIG. 7, FIG. 8, and FIGS. 9A-9B) may be facilitated by receiving user input corresponding to an approximate wound boundary, and performing operations based thereon to identify the boundary and obtain measurements thereof. Such exemplary embodiments for identifying and measuring a wound boundary may be performed alternatively or in addition to the contour detection described in FIG. 7, and are described below and with reference to FIGS. 12-13. Generally, a user interface is provided which enables a user to define, via an input device, an approximate boundary of the wound over an image of the wound. The boundary may comprise any shape and does not have to correspond accurately to the shape of the wound depicted in the image. The user may optionally further indicate regions of interest, as described above. Operations subsequently executed by an imaging device or computer upon which the user interface is provided include labeling pixels outside the approximate user-defined boundary as background, and labeling pixels that are within the boundary as foreground. Other pixels may be labeled either as background or foreground. For example, pixels outside the user-defined boundary can be labeled an obvious background (BG), and pixels inside the user-defined boundary may be categorized into three categories comprising possible background (PBG), possible foreground (PFG), and obvious foreground (FG). The boundary is identified using a combination of processing techniques including image segmentation by iterative minimization, border matting, foreground estimation, and other operations including those performed in the GrabCut method (https://cvg.ethz.ch/teaching/cvl/2012/grabcut-siggraph04.pdf).

FIGS. 12A-12C depict an exemplary image of a wound with a user-defined boundary and foreground and background regions determined based thereon. For example, FIG. 12A depicts an exemplary image 1200 of a wound 1220. The image 1200 may have been acquired using the same device/system components that are used for real-time imaging of wounds as described herein, or at least using common imaging conditions such as an excitation (or illumination) light type and frequency, filters, etc. The image 1200 may be acquired in real-time using imaging hardware coupled to the analysis modules described herein. Alternatively or in addition, the image 1200 may be acquired from the imaging hardware and transmitted to a computer that performs the disclosed operations, or from an external source, such as a database or network. Generally, the image 1200 is initially acquired using an RGB camera or sensor, resulting in an RGB raw image. Other systems for acquiring images in various formats are possible. Further, image 1200 depicts one or more wounds 1220, surrounding tissue surfaces, and characteristics thereof. For example, the wound 1220 can include any injury or damage to a surface of an organism, such as a cut, burn, scrape, surgical incision, ulcer, etc. A wound can expose an area underneath skin, including blood, connective tissue, muscles, bone, etc. In an exemplary embodiment, a wound 1220 can include a surgical cavity.

FIG. 12B depicts a user-defined boundary 1222 that is provided by a user of a device upon which a user interface for receiving a touch-based input is provided. For example, the user-defined boundary 1222 may be provided to be included as part of training image data, along with other characteristics of wound 1220 such as fluorescence data, RGB color data, and other pixel values and bacterial presence. Alternatively or in addition, the user-defined boundary 1222 may have been provided during real-time imaging of a wound on a patient, and may be input via a touch-sensitive screen of a wound imaging and analysis device, such as the above-described MolecuLight i:X® device developed by MolecuLight®. In either case, as described herein, the user-defined boundary 1222 need not follow the shape of the wound 1220, and may simply be an approximation of a region of image 1200 that contains wound 1220.

FIG. 12C depicts foreground and background regions determined based on an analysis of the image 1200 and the user-defined boundary 1222. As shown in FIG. 12C, pixels outside the user-defined boundary 1222 can be labeled an obvious background 1224, and pixels inside the user-defined boundary 1222 may be segmented into three segments comprising possible background 1226, possible foreground 1228, and obvious foreground 1230. These regions may be detected using a combination of processing techniques including image segmentation by iterative minimization, border matting, foreground estimation, and other methods described in the open source GrabCut algorithm cited above, thereby enabling the user defined boundary 1222 to be irregular or incomplete. Further, an adjustment mechanism may be provided via a user interlace, enabling the user to adjust a thickness or position of each of segment 1224, 1226, 1228, 1230. For example, a slider may be provided to adjust a segmentation variable, which results in expansion or contraction of the segments 1224, 1226, 1228, 1230 until the desired or accurate level is reached. Thus, facilitating such boundary detection can enhance the other operations described above, such as detecting areas of interest, quantifying metrics of interest, etc.

In additional exemplary embodiments, dimensions of the wound boundary determined by the above segmentation can be determined via a sequence of operations performed on the determined boundary. For example, to determine the length of the wound, first a bounding box is drawn around the determined wound boundary. Subsequently, one or more intersection points are determined between the wound boundary and the bounding box. The one or more intersection points correspond to the extreme points of the length. A distance is measured between each intersection point or extreme point, and a maximum of the distances is determined to be the length of the wound. Then for the width, a perpendicular slope is determined based on the two intersection points defining the length, and the contour points along the perpendicular slope are iterated from a first extreme point to the last. At each iteration, a perpendicular line is constructed, and a bitwise operation performed for each perpendicular line and the wound boundary. The resulting plurality of lines are determined with one or more line-finding techniques, the width of each line determined as vectors, and a maximum value is found from among the plurality of vectors. The maximum value corresponds to the width of the wound. Further, an area of the wound can be computed using a line integral technique such as Green's theorem. Further, although the length, width, and area values are determined in pixels, based on the image itself, they may be converted to a physical value (e.g. mm, $mm^2$) based on by detecting the two stickers placed around the wound and computing the pixel to mm ratio.

As described herein, a marker or sticker placed on a patient's body can be used to orient a field of view of a camera, to facilitate registration, to find co-located features, to align images, identify distances, and re-orient images. For example, an image is acquired after placing two distinct markers or stickers at opposite ends of a wound, the acquired image is processed to detect the stickers and their diameters (i.e., the pixel/mm ratio for each sticker obtained by dividing its diameter measured in pixels by its physical length), and the pixel/mm ratio for the wound is determined to be the average of the two stickers' pixel/mm ratio. In further exemplary embodiments, a combination of one or more of a color of a sticker, a size of a sticker, a shape of a sticker, an image or marking on a sticker, and combinations of different stickers may be used to indicate different types of wounds or patients, or to trigger different types of co-registration and analyses thereof such as, for example, automatic file association and storage of images containing certain stickers. In exemplary embodiments, stickers of a known size, shape, color and/or pattern, or a known image, marking, or motif are utilized.

However, relying solely on a color of a sticker or marker may yield unpredictable results, since lighting can change even if the same imaging apparatus is used. Thus, additional properties of a sticker, such as a shape, circularity, elongation, area, etc. can be utilized to differentiate the stickers from other objects in an image or field of view. Generally, these properties may depend on how the stickers appear in an image. Thus, operations described herein include utilizing a dataset of known images to tune or train how these properties are analyzed. In an exemplary embodiment, various types and shapes of stickers are manually segmented and properties of each segment of stickers measured and input into a training algorithm. Similar to the training dataset for wound images described above, such manual segmentation facilitates generation of ground truth by carefully isolating stickers from their background. Subsequently, an objective determination of the performance of the dataset can be made. Further, these operations can be performed in real time, i.e. during visualization and analysis of a wound using the imaging devices described above, enabling provision of real-time feedback improving the efficacy of the imaging devices and determination of wound size and area.

Figure 13A:
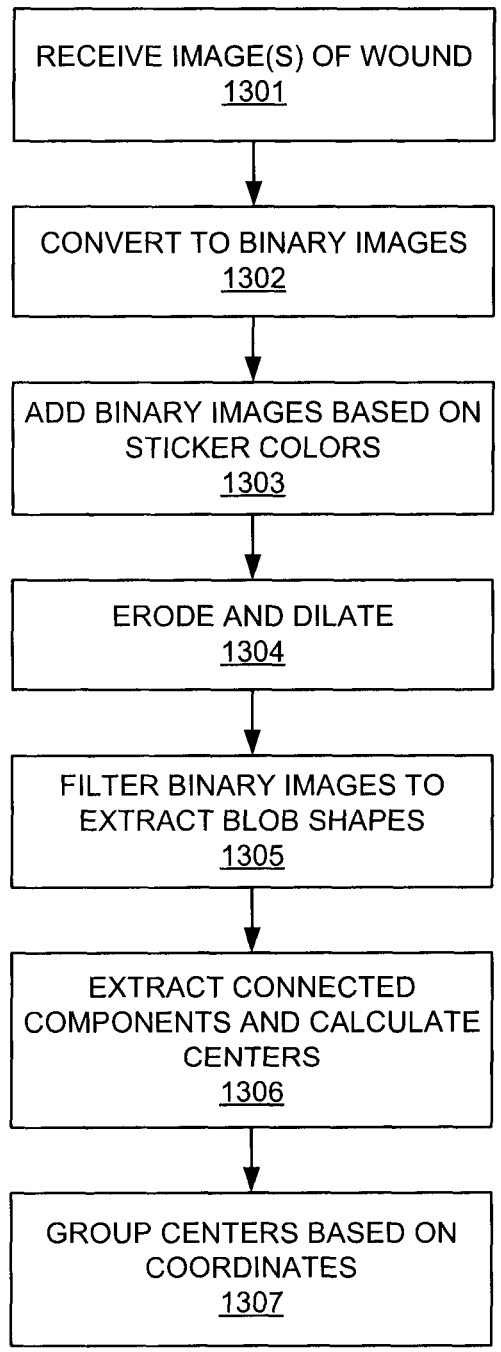
FIG. 13A-B depict an exemplary method for identifying stickers in a wound image and illustration thereof.

FIG. 13A depicts a method for identifying stickers in a wound image, according to an exemplary embodiment. Components for performing the method of FIG. 13A, including devices and systems, are further described with reference to FIGS. 2-3. However, it should be noted that the operations described in FIG. 13A may be performed by any device or system, with necessary adjustments being apparent to those having ordinary skill in the art in light of this disclosure. At operation 1301, an image of a wound is received. The image may have been acquired using the same device/system components that are used for real-time imaging of wounds as described herein, or at least using common imaging conditions such as an excitation (or illumination) light type and frequency, filters, etc. The image may be acquired in real-time using imaging hardware coupled to the analysis modules described herein. Alternatively or in addition, the image may be acquired from said imaging hardware and transmitted to a computer that performs the disclosed operations, or from an external source, such as a database or network. Further, the image depicts one or more wounds, surrounding tissue surfaces, and characteristics thereof. For example, the wound can include any injury or damage to a surface of an organism, such as a cut, burn, scrape, surgical incision, ulcer, etc. A wound can expose an area underneath skin, including blood, connective tissue, muscles, bone, etc. In an exemplary embodiment, a wound can include a surgical cavity.

At 1302, the image is converted to one or more binary images by applying thresholding with several thresholds from a minimum inclusive threshold to a maximum exclusive threshold, and a distance threshold step performed between neighboring thresholds. In an exemplary embodiment, the binary images may be generated using chroma masking operations as described above with reference to FIG. 6. Further, at 1303, additional binary images are added to the binary images generated in 1302, with the additional binary images being based on a thresholding operation using a color of the stickers. At 1304, erode and dilate operations are performed to remove noise. Similar to the operations described in FIG. 6, this step includes applying a spatial filter to the binary images to remove unwanted pixels such as outliers, and sparse segments, and applying a dilation spatial filter to counter some of the negative effects of erosion and rejoin smaller clusters that survived the erosion.

At 1305, the binary images are filtered using a plurality of criteria to extract blob-shape objects from the background. In other words, the stickers are correctly identified by filtering out the detected blobs based on their shape. Thus, the filtration operations include calculating all the moments up to the third order, and then performing several filtrations of returned blobs based on a plurality of criteria that are tuned to detect stickers accurately and reliably. In an exemplary embodiment, the plurality of criteria include an area, a circularity, a ratio of minimum inertia to maximum inertia, a convexity, a compactness, a binary color, and/or an ellipticity. For example, extracted blocks may be required to have an area between a minimum (inclusive) and a maximum (exclusive); a circularity between a minimum and a maximum (computing using, for example, an arclength formula); a ratio of the minimum inertia to maximum inertia between a minimum and a maximum (which provides a measurement of elongation); an area of the blob divided by an area of the blob's convex hull (i.e. convexity) between a minimum and a maximum, a compactness between a minimum and a maximum. Further, an intensity of each binary image may be compared at the center of a blob to a color value of the blob, and different values are filtered out (since this is a binary image, the color filtration process is different than filtering the image based on RGB/CIELAB/HSV color space values as described above). Finally, an area measured by the first moment is compared with an area of the ellipse, and blobs with a value greater than a maximum are filtered out.

Then, at 1306, connected components are extracted from each binary image and their centers are calculated. At 1307, centers from several binary images are grouped based on their coordinates, with close centers form one group corresponding to one blob. This may be determined using a minimum distance between blobs parameter, or other technique such as the open-source OpenCV simpleblobdetector (https://docs.opencv.org/3.3.1/d0/d7a/classcv_1_1SimpleBlobDetector.html). Each of these parameters may be tuned by an operator, depending on the desired outcome. For example, the parameters may be tuned to effectively separate the stickers from other blob-shaped objects. One or more standardized images may be generated to enable measurement of all parameters from a single image. Such an image may be referred to as a parameter tuning image, wherein the stickers in the parameter tuning image are manually segmented and intensity, circularity, inertia, area, convexity, ellipticity, compactness, and minimum distance measured using the techniques identified above. The minimum and maximum of these measurements can be stored and used as optimal values to detect stickers in subsequent images. Further, the stored tuned parameters may be adjusted continuously as the ground truth database gets larger.

Figure 13B:
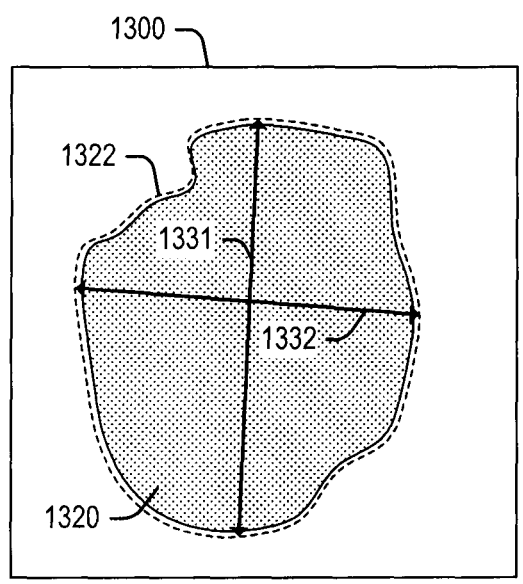

The result of this method provides a set of 2-dimensional points (i.e. contours) per blob. Further, the set of contours can be merged and displayed on the source image. Each merged contour represents the boundary of a single sticker, and can be determined by approximating the final contours by approximating a curve with another curve with less vertices so that the distance between them is less or equal to the specified precision, given the set of 2D points per blob. Final centers of each blob are determined, a looping operation is performed to loop through the contours and fit an ellipse around them, to return a rotated rectangle in which the ellipse is inscribed. Additionally, the major and minor axes of each blob are obtained and stored. Finally, an ellipse and a rectangle are drawn around each sticker using rotated rectangle computed in the previous step. FIG. 13B illustrates an image 1300 of a wound 1320, including a boundary 1322 determined as described above, and major axis 1331 and minor axis 1332 displayed on the wound image 1300.

To enable real-time processing and visualization, e.g. of a video comprising a series of images (i.e. frames), each frame may be retrieved from a storage buffer and processed in real-time. For example, an entire first frame maybe processed to locate the stickers, and to lower the consumption of computational resources, a small region-of-interest may be defined around each sticker detected in the first frame, and subsequent frames may be processed based on the defined regions of interest rather than processing the entire frame.

As described above, a validation dataset may be utilized to evaluate the performance of the above sticker detection methods. For example, a validation process for detecting stickers may include manually segmenting images to create a ground truth used to quantitatively evaluate the detection method. Metrics such as a dice metric, an area, and a Hausdorff distance can be useful in validating the accuracy of the segmentation. A dice coefficient is determined to measure the extent of spatial overlap between two binary images, and its values can range between 0 (no overlap) and 1 (perfect agreement), based on the following equation:

$$DSC = \frac{2TP}{2TP + FP + FN}$$

where TP, FP, and FN refer to true positive, false positive, and false negative respectively. If the segmented region is labeled as 1 and background as 0, a true positive means the total number of pixels which have the value 1 in both segmented and ground truth images, a false positive means the total number of pixels which appear as 1 in segmented image but 0 in the ground truth, and a false negative means the total number of pixels which appear as 0 in segmented image but 1 in ground truth Further, an Area Similarity (AS) operation utilizes the following equation:

$$AS = 1 - \frac{||Area_{seg.}| - |Area_{truth}||}{|Area_{seg.}| + |Area_{truth}|}$$

Wherein, AS=1 for a perfect segmentation and AS~0 for poor segmentations.

Further, an Average Hausdorff Distance (AHD) between two finite point sets of A and B can be defined by the following equation:

$$AHD(A, B) = \max(d(A, B), d(B, A))$$

where $d(A, B) = \frac{1}{N} \sum_{a \in A} \min_{b \in B} ||\text{Euclidean distance between } a \text{ and } b||$ A Sobel edge detection operation may be used to define the A and B sets as the points on the edges of the stickers in both ground truth and automatically segmented images.

Thus, the above methods facilitate sticker detection by utilizing combinations of sticker color, sticker shape, and sticker size to facilitate determination of a size and orientation of a wound in a wound image. Further, a camera, such as a surgical camera, can be co-registered with anatomical locations based on stickers. Gyroscopes and self-orienting software incorporated into the surgical cameras can be used to co-register the camera field of view with the surgical field, to spatially identify features of a surgical cavity or a wound, and to enhance a real-time view provided to a surgeon or other operator of such a camera. Further, each of these methods can be tuned to be executed at approximately 27 frames per second, to provide a real-time feedback for the surgeon/operator. In an exemplary embodiment, the methods are tuned to a minimum of 27 frames per second, and potentially frames rates above 27 frames per second.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

It will be apparent to those skilled in the art that various modifications and variations can be made to the devices and methods of the present disclosure without departing from the scope of its teachings. Other embodiments of the disclosure will be apparent to those skilled in the art from consideration of the specification and practice of the teachings disclosed herein. It is intended that the specification and embodiments described herein be considered as exemplary only.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

What is claimed is:

1. A computer-implemented method for wound analysis, the computer-implemented method stored on a computer-readable medium and comprising logical instructions that are executed by a processor to perform operations comprising:
    receiving an image of a wound, the image comprising a plurality of pixels;
    determining at least one area of interest in the image based on at least an application of a chroma mask on a pixel-by-pixel basis to each of the plurality of pixels, the chroma mask being based on a histogram of pixel values;
    determining one or more contours of the at least one area of interest; and
    generating an output image comprising the one or more contours overlaid on the image;
    wherein the at least one area of interest comprises one or more wound characteristics.

2. The method of claim 1, wherein the one or more wound characteristics comprises a wound boundary, a wound size, a wound depth, a bacterial presence, a bacterial load, a wound temperature, a connective tissue presence, a blood presence, a bone presence, a change in tissue or cellular wound components, a vascularization, or a necrosis.

3. The method of claim 1, further comprising generating the histogram of pixel values based on a plurality of training images of one or more wounds, each of the plurality of training images containing at least one known area of interest, wherein the histogram of pixel values identifies unique spectral signatures for one of more of the wound characteristics.

4. The method of claim 3, wherein the at least one known area of interest is based, at least in part, on a swab or tissue biopsy analysis of the wound in the respective training image of the plurality of training images.

5. The method of claim 3, further comprising classifying the plurality of training images based on the at least one known area of interest.

6. The method of claim 3, wherein the histogram comprises a composite histogram based on a plurality of known areas of interest corresponding to the plurality of training images.

7. The method of claim 1, further comprising repairing the one or more contours from a concave shape to a convex shape.

8. The method of claim 1, further comprising acquiring the image of the wound using a wound imaging device.

9. The method of claim 1, wherein acquiring the image of the wound further comprises using an imaging device of a mobile communication device, the mobile communication device forming a portion of a handheld wound imaging and analysis device.

10. The method of claim 9, wherein receiving the image of the wound includes transferring image data from the imaging device of the mobile communication device to a processor of the handheld wound imaging and analysis device.

11. The method of claim 9, further comprising illuminating the wound with an excitation light source of the handheld wound imaging and analysis device configured to excite portions of the wound.

12. The method of claim 11, wherein illuminating the wound comprises illuminating the wound with an excitation light source.

13. The method of claim 12, wherein illuminating the wound further comprises illuminating the wound with an excitation light source having a wavelength of approximately 405 nm.

14. The method of claim 1, further comprising detecting at least one marker in the image, and registering the image based on the at least one detected marker.

15. The method of claim 14, wherein detecting the at least one marker further comprises converting the image into to one or more binary images based on application of one or more thresholds; generating and adding one or more additional binary images based on thresholding a color of one or more known markers; removing noise using erode and dilate operations; filtering the image using a plurality of shape-based criteria; extracting connected components from each binary image; calculating center coordinates of each connected component; and grouping the binary images based on the center coordinates.

16. The method of claim 15, wherein the plurality of shape-based criteria includes one or more of: an area, a circularity, a ratio of minimum inertia to maximum inertia, a convexity, a compactness, a binary color, and/or an ellipticity.

17. The method of claim 14, wherein registering the image further comprises co-registering the image with one or more standardized images, the one or more standardized images comprising manually segmented stickers having known intensities, circularities, inertias, areas, convexities, ellipticities, compactness, and/or minimum distances.

18. The method of claim 14, wherein the image comprises one of a plurality of frames of a real-time video, the method further comprising identifying the at least one marker by processing a first frame of the real-time video in its entirety, automatically defining a region of interest around each marker, and identifying each marker only within the respective region of interest in each subsequent frame from the plurality of frames.

19. The method of claim 1, further comprising receiving an input indicating an approximate wound boundary, and determining an actual wound boundary based on the input.

20. The method of claim 19, wherein determining the actual wound boundary comprises identifying and labeling pixels outside the approximate wound boundary as background pixels, and identifying and labeling pixels within the approximate wound boundary as one of: possible background pixels, possible foreground pixels, or obvious foreground pixels.

21. The method of claim 20, wherein identification of the pixels is based on segmentation, the segmentation comprising iterative minimization.

22. A system comprising:
an imaging device;
a processor coupled to the imaging device; and
a memory coupled to the processor, the memory configured to store computer-readable instructions that, when executed by the processor, cause the processor to perform operations on an image of a wound obtained using the imaging device, comprising:
accessing the image of a wound, the image comprising a plurality of pixels;
applying a chroma mask on a pixel-by-pixel basis to each of the plurality of pixels, the chroma mask being based on a histogram of pixel values;
generating a binary mask based on the application of the chroma mask, the binary mask identifying at least one area of interest on the image;
detecting one or more contours of the at least one area of interest to define at least one boundary of the at least one area of interest;
overlaying the one or more contours on the image to form a composite image identifying the at least one area of interest; and
outputting the composite image to a user of the imaging device in real time.

23. The system of claim 22, wherein the computer-readable instructions are further configured to cause the processor to perform operations comprising determining a presence of one or more colors within the image in any combination.

24. The system of claim 23, wherein determining the presence of the one or more colors further comprises processing the image through a plurality of user-defined thresholds and generating a color mask.

25. The system of claim 24, wherein the color mask indicates a presence of one or more target characteristics associated with the color combination.

26. The system of claim 25, wherein the one or more target characteristics comprise one or more of a bacterial presence, a bacterial colony, a wound size, a wound boundary, and a collagen proliferation.

27. The system of claim 22, further comprising a database to store the histogram of pixel values.

28. The system of claim 22, wherein the imaging device is an imaging device of a mobile communications device.

29. The system of claim 28, wherein the mobile communications device and the processor are contained within a housing of the system.

30. The system of claim 22, wherein the imaging device is communicatively coupled to the processor via a network.

31. A tangible non-transitory computer-readable medium to store computer-readable code that is executed by a processor to perform operations comprising:
  acquiring a plurality of red, green, and blue (RGB) images, the images comprising a plurality of pixels;
  utilizing a computer interface to mark known areas of interest on each of the plurality of images, the known areas of interest comprising one or more of a bacterial presence, a wound boundary, a collagen proliferation, and a wound size;
  converting each of the plurality of RGB images into a hue-saturation-value (HSV) color space;
  determining a histogram of HSV values for each of the plurality of RGB images, the histogram of HSV values identifying a unique spectral signature for each of the known areas of interest; and
  generating a composite histogram based on the histogram of HSV values for each of the plurality of RGB images;
  wherein the composite histogram is used to identify a plurality of unknown areas of interest in real time, in at least one wound image acquired on a wound imaging device, based on one or more unique spectral signatures.

32. The computer-readable medium of claim 31, wherein the processor further performs operations comprising generating the histogram of pixel values based on a plurality of training images of one or more wounds, each of the plurality of training images containing at least one known area of interest.

33. The computer-readable medium of claim 32, wherein the histogram comprises a first set of pixel values for pixels outside the at least one known area of interest, and a second set of pixel values for pixels inside the at least one known area of interest.

34. The computer-readable medium of claim 32, wherein the at least one known area of interest is based, at least in part, on a swab analysis of the wound in the respective training image of the plurality of training images.

35. The computer-readable medium of claim 32, wherein the processor further performs operations comprising classifying the plurality of training images based on the at least one known area of interest.

36. The computer-readable medium of claim 32, wherein the histogram comprises a composite histogram based on a plurality of known areas of interest corresponding to the plurality of training images.

37. A system comprising:
  a processor; and
  a memory coupled to the processor, the memory configured to store computer-readable instructions that, when executed by the processor, cause the processor to perform operations comprising:
    receiving or accessing an image of a wound or a tissue specimen, the image comprising a plurality of pixels;
    applying a chroma mask on a pixel-by-pixel basis to each of the plurality of pixels, the chroma mask being based on a histogram of pixel values and identifying at least one area of interest on the image;
    detecting one or more contours around the at least one area of interest; and
    overlaying the one or more contours on the image to form a composite image identifying the at least one area of interest; and
    outputting the composite image on a display device coupled to the processor.

38. The system of claim 37, wherein the image of the wound or tissue specimen is acquired using a first imaging device.

39. The system of claim 38, wherein the histogram of pixel values is based on a plurality of test images, the test images having been acquired using a second imaging device that is substantially equivalent to the first imaging device.

40. The system of claim 39, wherein the second imaging device has the same imaging components as the first imaging device.

41. The system of claim 37, wherein the area of interest comprises one or more wound characteristics, the one or more wound characteristics comprising wound size, wound boundaries, wound depth, wound temperature, changes in tissue and cellular wound components, vascularization, necrosis, and bacterial presence.

42. The system of claim 37, wherein the area of interest comprises one or more tissue characteristics, the one or more tissue characteristics comprising tissue components, a tumor size, a tumor edge, a tumor boundary, and a tissue vascularization.

43. A computer-implemented method for wound analysis, the computer-implemented method stored on a computer-readable medium and comprising logical instructions that are executed by a processor to perform operations comprising:
  receiving an image of a wound, the image comprising a plurality of pixels;
  detecting at least one marker in the image; and
  registering the image based on the detected at least one marker,
  wherein detecting the at least one marker in the image comprises:
    converting the image into to one or more binary images based on application of one or more thresholds on a pixel-by-pixel basis for each of the plurality of pixels;
    generating and adding one or more additional binary images based on thresholding a color of one or more known markers;
    removing noise using erode and dilate operations;
    filtering the image using a plurality of shape-based criteria;
    extracting connected components from each binary image;
    calculating center coordinates of each connected component; and
    grouping the binary images based on the center coordinates.

44. The method of claim 43 wherein the plurality of shape-based criteria includes one or more of: an area, a circularity, a ratio of minimum inertia to maximum inertia, a convexity, a compactness, a binary color, and an ellipticity.

45. The method of claim 43, wherein registering the image further comprises co-registering the image with one or more standardized images, the one or more standardized images comprising manually segmented stickers having known intensities, circularities, inertias, areas, convexities, ellipticities, compactness, and/or minimum distances.

46. The method of claim 43, wherein the image comprises one of a plurality of frames of a real-time video, and wherein detecting the at least one marker further comprises processing a first frame of the real-time video in its entirety, automatically defining a region of interest around each marker, and identifying each market only within the respective region of interest in each subsequent frame from the plurality of frames.

\* \* \* \* \*